United States Patent [19]

Murphy et al.

[11] Patent Number: 5,544,654
[45] Date of Patent: Aug. 13, 1996

[54] VOICE CONTROL OF A MEDICAL ULTRASOUND SCANNING MACHINE

[75] Inventors: Sean Murphy, Fremont; Daniel E. Need, Palo Alto, both of Calif.

[73] Assignee: Acuson Corporation, Mountain View, Calif.

[21] Appl. No.: 471,373

[22] Filed: Jun. 6, 1995

[51] Int. Cl.$^6$ .................................................. A61B 8/00
[52] U.S. Cl. ................................. 128/660.07; 395/924
[58] Field of Search ........................ 128/660.01, 660.04, 128/660.07, 653.1; 364/413.13, 413.15, 413.25, 413.02; 395/2, 2.55, 2.59, 2.79, 2.84, 924

[56] References Cited

U.S. PATENT DOCUMENTS

| | | | |
|---|---|---|---|
| 5,261,404 | 11/1993 | Mick et al. | 128/660.07 |
| 5,267,174 | 11/1993 | Kaufman et al. | 364/479 |
| 5,345,538 | 9/1994 | Narayannan et al. | |

*Primary Examiner*—George Manuel
*Attorney, Agent, or Firm*—Majestic, Parsons, Siebert & Hsue

[57] ABSTRACT

By using a structured vocabulary where subsets of a total large vocabulary are used for speech recognition to control an ultrasound machine, recognition performance is improved. Where the subsets of voice commands are selected to fit the state of the ultrasound machine so as to afford complete control of the machine, little or no degradation of the control of the machine will result. A two-way communication link between the voice control system and the ultrasound machine permits the monitoring of the state of the ultrasound machine so that subsets of the total vocabulary may be made active. From knowledge of the state of the ultrasound machine, dynamic macros may be implemented for streamlined control of the ultrasound machine. A two-way communication link between the voice control system and the ultrasound machine permits simultaneous control by means of, but not limited to, voice control, keyboard and foot-switch.

24 Claims, 6 Drawing Sheets

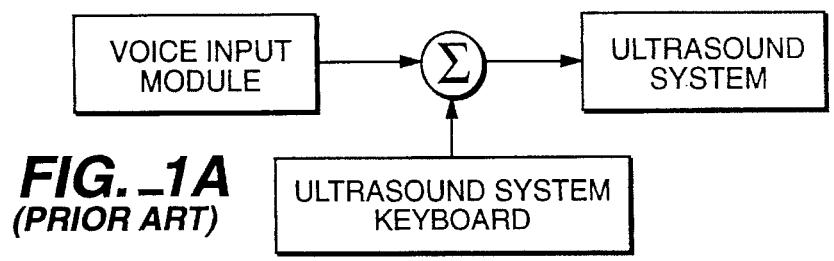
FIG._1A
*(PRIOR ART)*
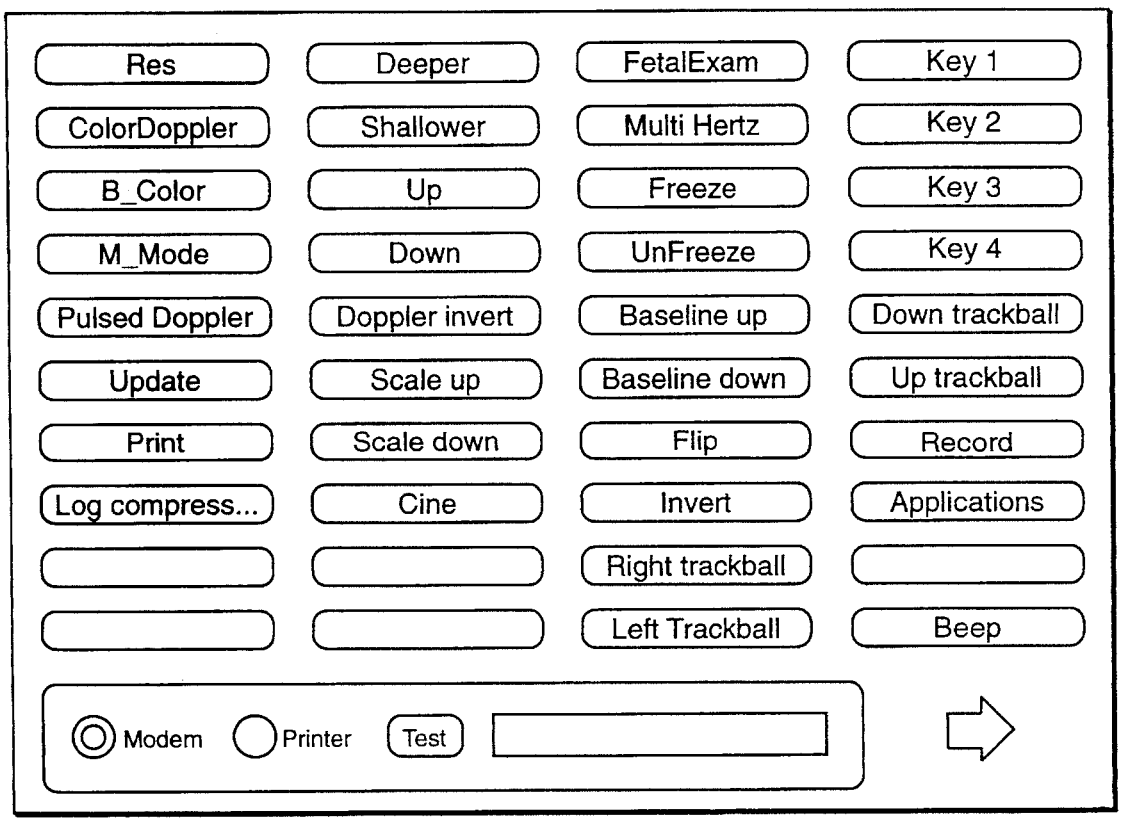
FIG._1B
*(PRIOR ART)*
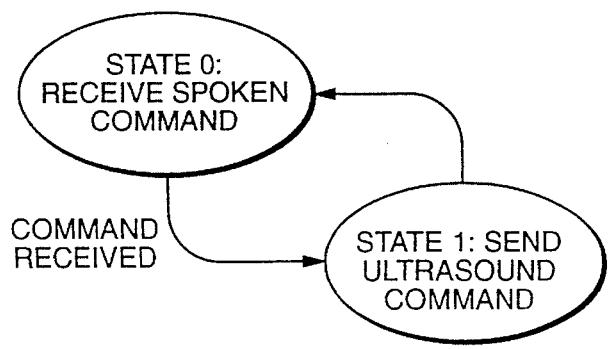
FIG._2
*(PRIOR ART)*

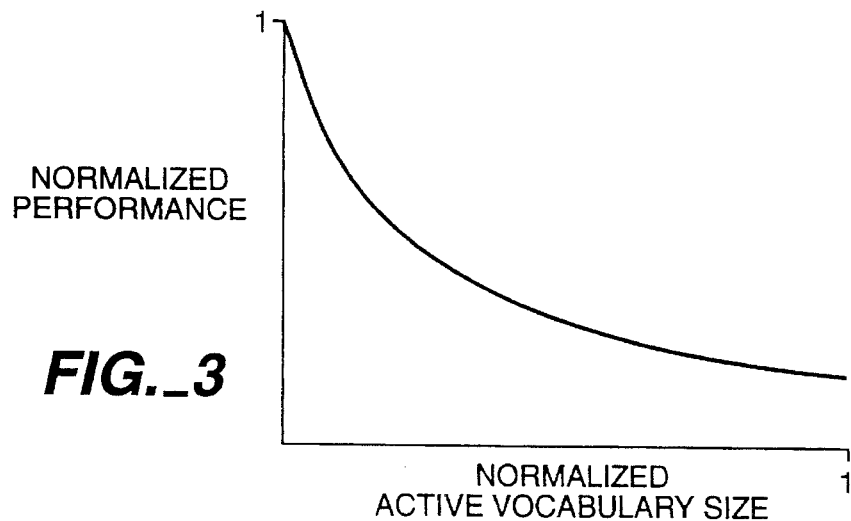
FIG._3
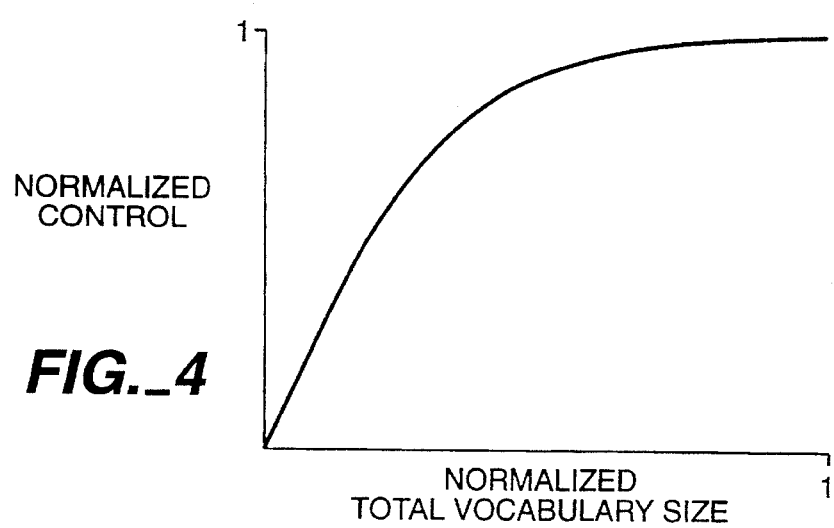
FIG._4
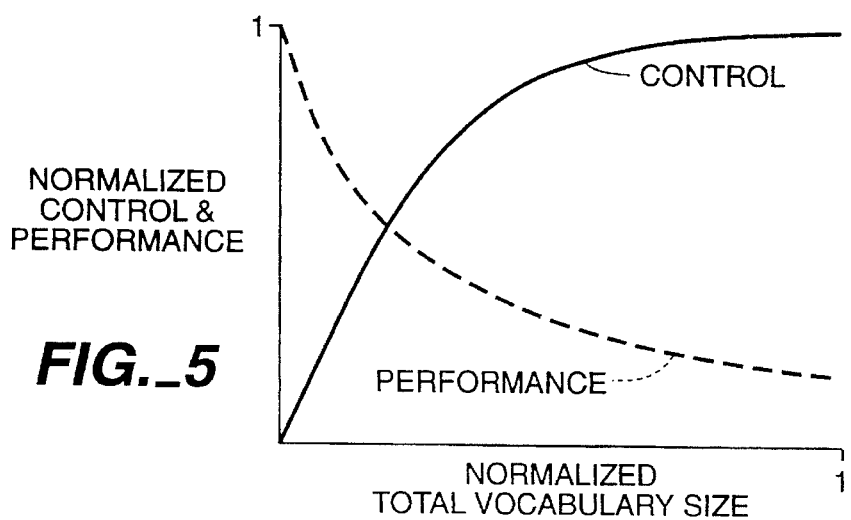
FIG._5

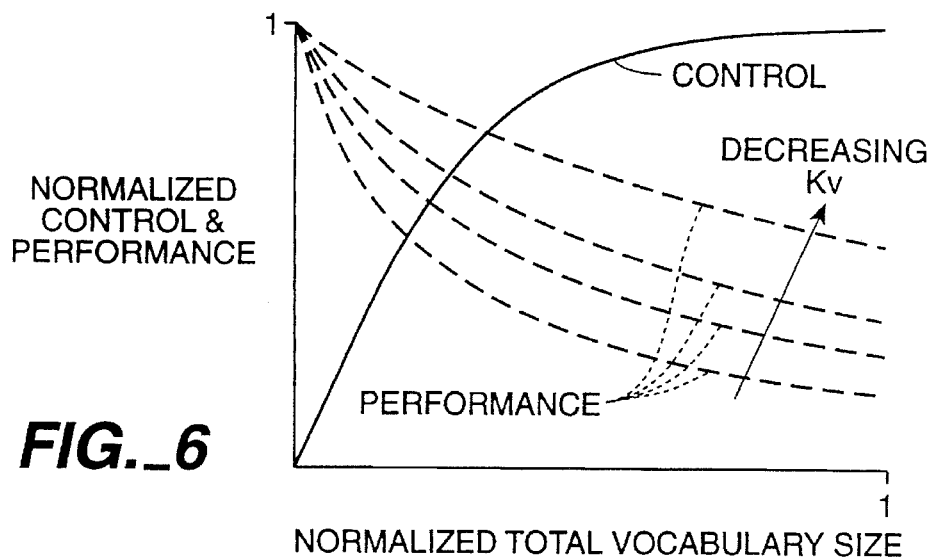
FIG._6
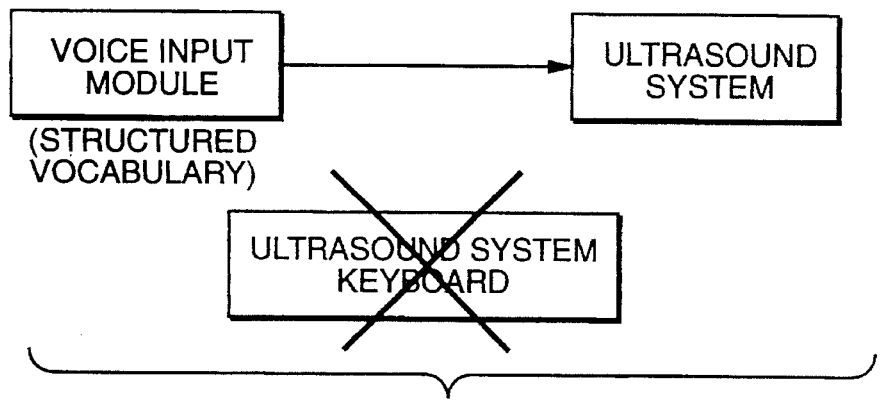
FIG._7
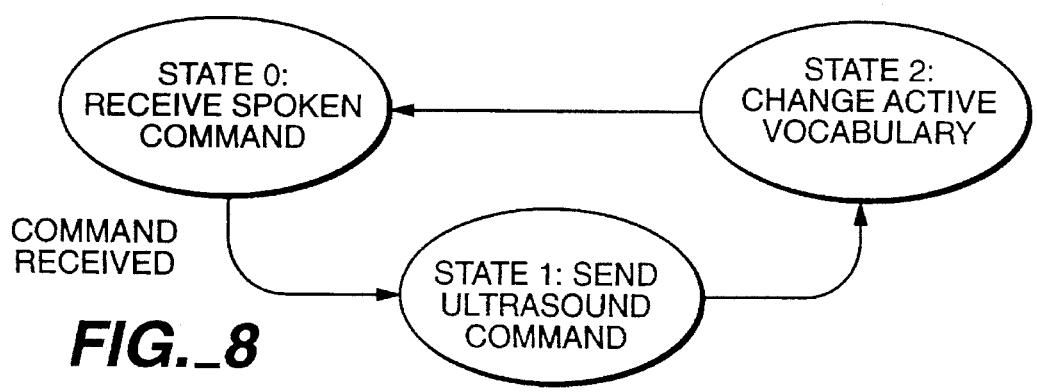
FIG._8

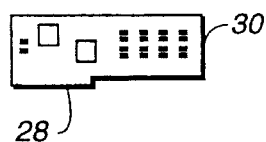
FIG._9A
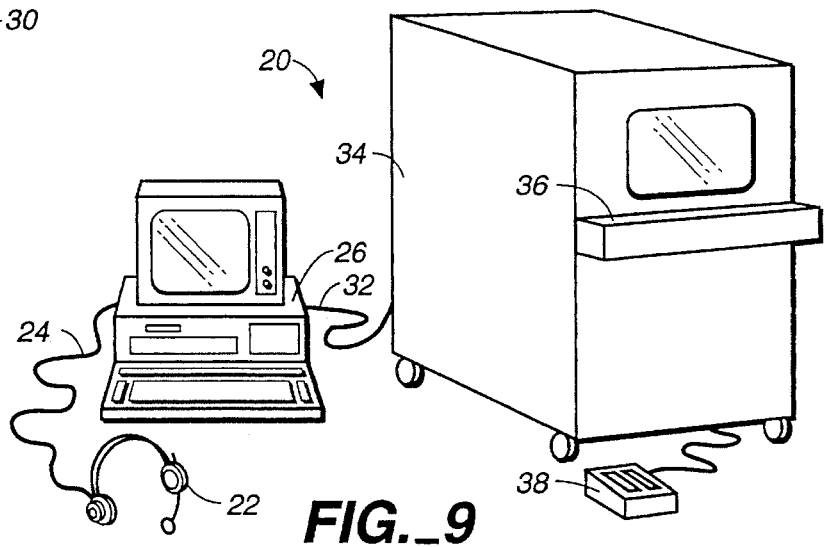
FIG._9
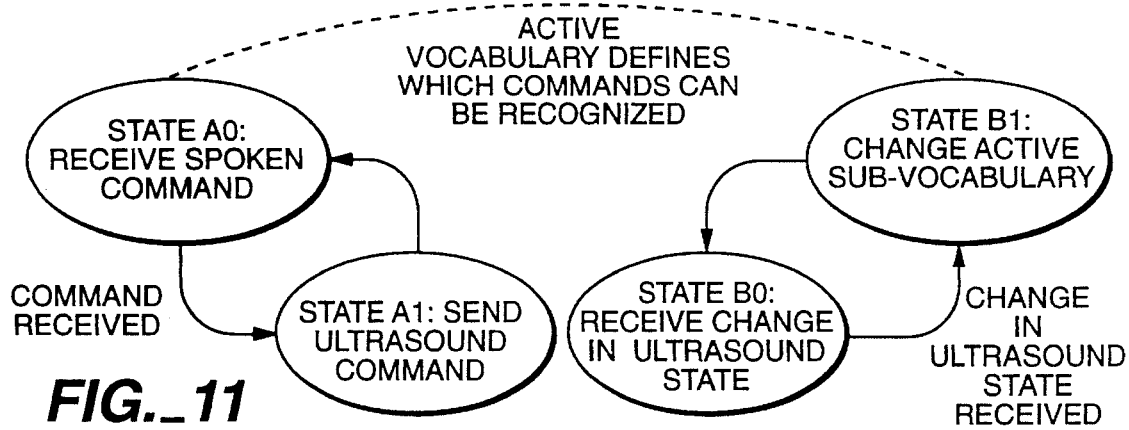
FIG._11
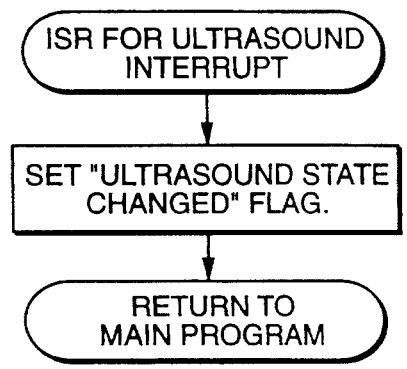
FIG._12
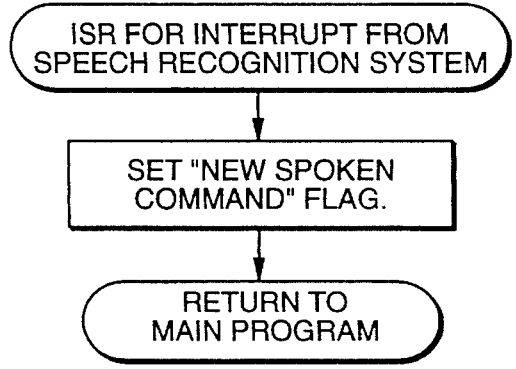
FIG._13

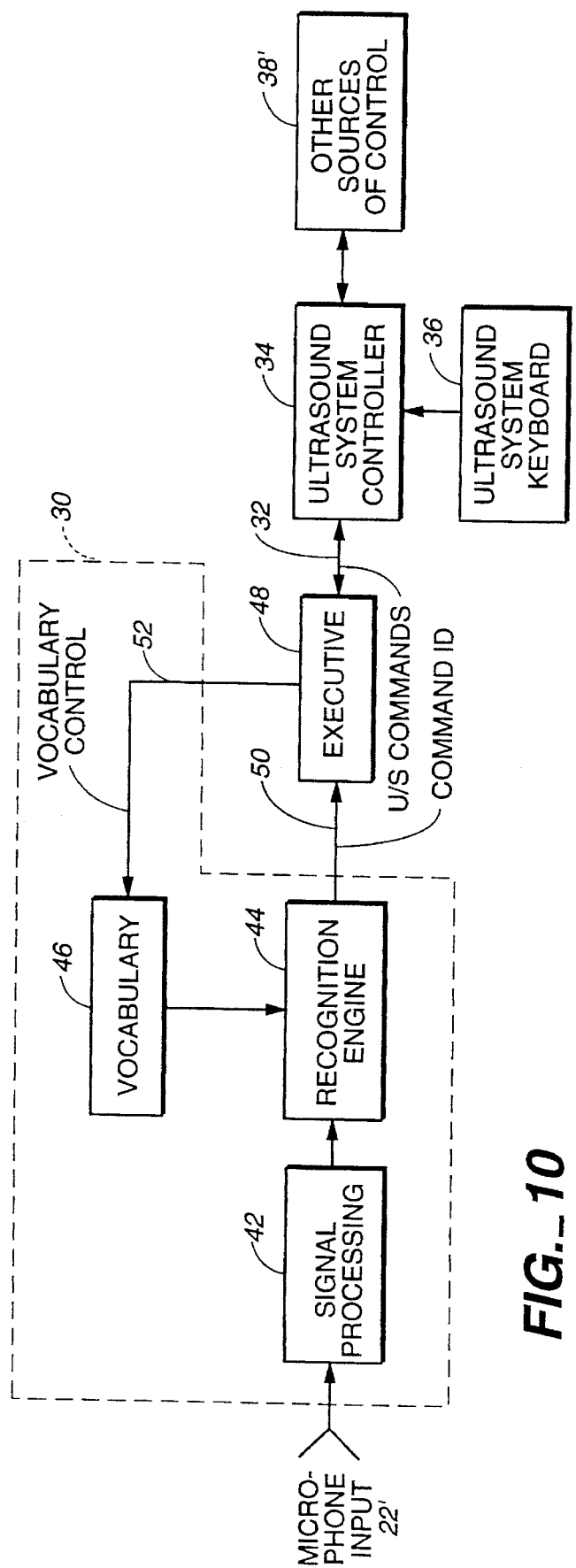
FIG._10

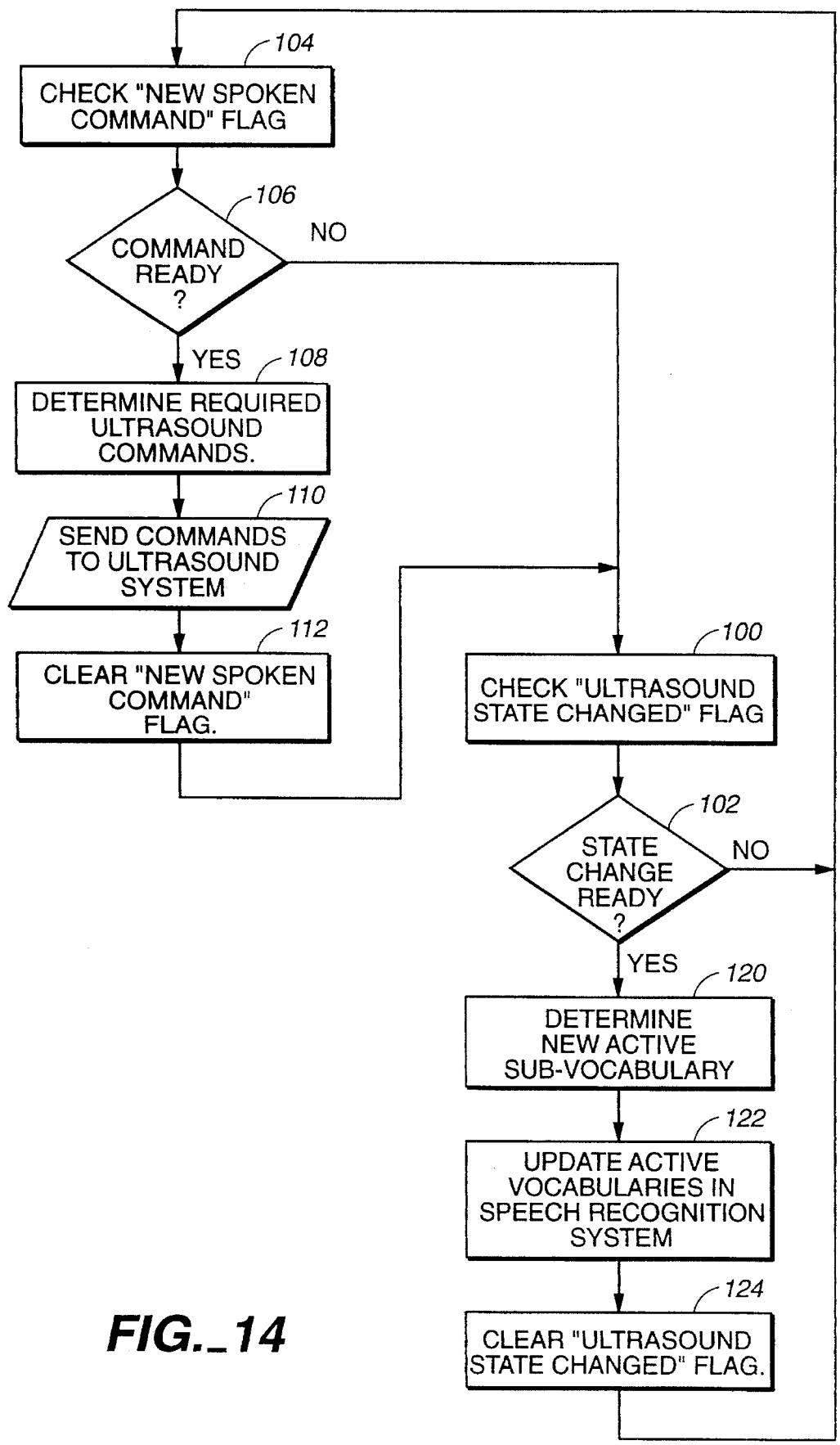
FIG._14

VOICE CONTROL OF A MEDICAL ULTRASOUND SCANNING MACHINE

BACKGROUND OF THE INVENTION

This application is directed in general to voice control of medical ultrasound machines. This application is directed in particular to a voice control system with a structured recognition scheme to improve speech recognition performance without significantly compromising control of the ultrasound machine; and to a voice control system where the status of the ultrasound machine is taken into account in the control scheme.

Old Methods

Currently, several other methods exist for controlling the ultrasound machine in situations in which the keyboard alone is insufficient or inconvenient. These methods include:
(1) foot-switch;
(2) an extra assistant; and
(3) limited voice control.

Foot-switch

A foot-switch attached to the ultrasound machine allows the operator to depress a small number of keys (typically two) by operating the switches with his or her feet. The keys on the foot-switch can be defined by the operator to be the most critical functions that are necessary. This provides limited control of the ultrasound machine.

An Assistant

An additional individual assists with the examination, controlling the keyboard of the ultrasound machine in response to the spoken commands from the doctor or sonographer conducting the examination.

Limited Voice Control

A limited voice control system has been implemented which provides the operator the ability to verbally depress some of the keys of the keyboard by spoken commands. Such a system can be diagrammed as in FIG. 1A. The voice input module recognizes a limited vocabulary of spoken commands. This vocabulary allows the operator to send a subset of the commands that can also be sent by the keyboard. Commands can be sent to the ultrasound system by the keyboard or by the voice input module.

FIG. 1B illustrates the total vocabulary of possible voice commands on a screen of a computer monitor of the voice input module in the above-described voice control system. When a spoken voice command is recognized as one of the commands in the vocabulary shown in FIG. 1B, the voice control system converts the received voice command into corresponding keystroke commands which are applied as control signals to the ultrasound machine.

In this design, the voice input module operates independently of the ultrasound system. It can only send commands to the ultrasound system. There is no mechanism by which the ultrasound machine can communicate commands or information back to the voice input module to assist in the process of recognizing the spoken commands. A state diagram to represent the control flow in such a voice input module is shown in FIG. 2.

Disadvantages of Old Methods

All of these existing methods have distinct disadvantages in their inability to provide convenient and extensive remote control of the ultrasound machine.

Foot-switch

The foot-switch solution is limited in several ways. Primarily, it cannot provide broad control of the ultrasound machine. The operator must select which functions are to be controlled by the foot-switch based on the immediate needs. Only that limited subset of functionality of the machine can be accessed by means of the foot-switch.

A second limitation of the foot-switch is that many operators find it to be physically awkward to use in difficult scanning environments.

An Assistant

The primary disadvantage of having an assistant help with conducting an ultrasound examination is that the cost of the examination is increased. An additional disadvantage is the possibility of miscommunication between the sonographer conducting the examination and the assistant.

Limited Voice Control

The above-described voice control system is also disadvantageous for reasons explained below, in the "Detailed Description of the Preferred Embodiments."

None of the above-described systems for controlling the ultrasound machine is entirely satisfactory. It is therefore desirable to provide a voice control system which avoids the disadvantages of the various conventional systems.

SUMMARY OF THE INVENTION

This invention enables voice control to be used as a means of controlling an ultrasound machine simultaneously with the keyboard or other methods of machine control. The control provided is such that it allows difficult examinations to be mostly conducted without resorting to the keyboard to control the ultrasound machine. Such a capability might be used to:
(1) simplify difficult examinations;
(2) reduce the occupational health problems from scanning in physically awkward situations;
(3) reduce the number of sonographers and doctors required to conduct some difficult examinations; and
(4) obviate the need to microposition the ultrasound machine during the course of an examination.

This invention stems from the understanding that, while many factors contribute to the performance of a speech recognition system, the performance in terms of speed of response and recognition accuracy can be related inversely to the number of words in the vocabulary against which the voice input module is recognizing the spoken commands. If the entire vocabulary of possible commands is continually active, the designer is forced to choose between using a small vocabulary to enhance recognition performance at the expense of reduced ability to control the machine, or using a large vocabulary for more complete control over the machine while compromising the recognition performance. This invention teaches that by selecting different sub-groups of commands smaller in number than the entire group for controlling the machine, recognition performance can be enhanced without significantly compromising the completeness of control over the ultrasound machine, and while still allowing voice commands to be used in conjunction with other methods of machine control. Since the invention is applicable to non-verbal voice commands as well as verbal voice commands, the invention is summarized herein below generically in terms of "groups" and "sub-groups" of voice commands; although the preferred embodiment below is illustrated by reference more specifically to "vocabularies" and "sub-vocabularies" of verbal commands. The terms "ultrasound machine", "medical ultrasound machine", "ultrasound system", and "medical ultrasound system" are used interchangeably herein.

Therefore, one aspect of the invention is directed towards a method for voice activation of an ultrasound system using a plurality of voice commands. The method comprises providing a group of voice commands for controlling the ultrasound system. The group includes more than one sub-group of voice commands, wherein each of said sub-groups contains fewer number of voice commands than the group. The method further comprises selecting at least one of said sub-groups; deriving a signal from a spoken voice command using said selected at least one sub-group; and applying the signal to the ultrasound system to control the system.

Another aspect of the invention is directed towards an apparatus for voice activation of an ultrasound system having a plurality of voice commands, comprising means for providing a group of voice commands for controlling the ultrasound system, said group including more than one sub-group of voice commands, wherein each of said sub-groups contains fewer number of voice commands than the group. The apparatus further comprises means for selecting at least one of said sub-groups; means for deriving a signal from a spoken voice command using said selected at least one sub-group; and means for applying said signal to the ultrasound signal to control the system.

Knowledge of the state of the ultrasound machine is often important in voice control of the ultrasound system. When the state of the ultrasound system is such that a smaller group of voice commands is adequate for control of the system, then only such sub-group of commands needs to be used in the speech recognition. This allows the recognition performance to be enhanced without compromising control of the system. In other cases, the state of the ultrasound system may be such that a command or commands different from one obtained from a strict translation of the spoken voice command may need to be applied to accomplish the intended purpose of the spoken voice command. In such event, it is advantageous for the voice control system to know the actual state of the ultrasound machine.

Thus, another aspect of the invention is directed towards a method for voice activation of an ultrasound system, comprising the steps of providing a group of commands for controlling the ultrasound system and determining the actual state of the ultrasound system. The method further comprises deriving at least one signal from a spoken voice command using said group and based on the actual state of the ultrasound system; and applying the at least one signal to the ultrasound system.

Another aspect of the invention is directed towards an apparatus for voice activation of an ultrasound system, comprising means for providing a group of commands for controlling the ultrasound system; means for determining the actual state of the ultrasound system; means for deriving at least one signal from a spoken voice command using said group and based on the actual state of the ultrasound system; and means for applying the at least one signal to the ultrasound system.

BRIEF DESCRIPTION OF THE DRAWINGS

FIG. 1A is a block diagram of a conventional voice control system controlling an ultrasound system.

FIG. 1B is an image of the screen of a computer monitor of the voice input module of FIG. 1A to illustrate the different voice commands that can be recognized for controlling the ultrasound system.

FIG. 2 is a state diagram of the voice input module of FIG. 1A.

FIG. 3 is a graphical illustration of recognition performance as a function of active vocabulary size.

FIG. 4 is a graphical illustration of the completeness of control of the ultrasound system as a function of total vocabulary size.

FIG. 5 is a graph to illustrate the trade-off between recognition performance and completeness of control where a flat vocabulary is used.

FIG. 6 is a graph illustrating the trade-off between recognition performance and completeness of control with a structured vocabulary.

FIG. 7 is a block diagram of the voice control system where the voice input module is the only mode of control for the ultrasound system and where a structured vocabulary is employed.

FIG. 8 is a state diagram of control flow in the voice input module of FIG. 7.

FIGS. 9 and 9A are a diagram of a voice activation system for controlling an ultrasound machine to illustrate the invention.

FIG. 10 is a functional diagram illustrating the operation of the system of FIG. 9.

FIG. 11 is a diagram of control flow in the Executive portion of the voice control system of FIG. 10 to illustrate the preferred embodiment of the invention.

FIGS. 12 and 13 are diagrams of interrupt service routines to further illustrate the operation of the Executive portion of the voice control module of FIG. 10.

FIG. 14 is a flow chart illustrating the operation of the Executive portion of the voice control module of FIG. 10.

For simplicity in description, identical components or processing steps are referred to by the same numerals in the different figures of this application.

DETAILED DESCRIPTION OF THE PREFERRED EMBODIMENTS

Before the invention is described, it is useful to further discuss the drawbacks of the conventional limited voice control system briefly described above. For this, it is first necessary to understand some of the compromises inherent in the design of a practical speech recognition system for machine control.

At least two measures of the quality of a complete voice control system are particularly significant:

the recognition performance;

and the completeness of control over the target machine.

The recognition performance of a practical speech recognition system is a combination of both its speed of response to a spoken command and the accuracy or percentage of responses which are correct. Defined in this manner, a system's recognition performance is related inversely to the number of words in the active vocabulary, the vocabulary against which the voice input module is recognizing the spoken commands. This relationship can be displayed graphically as in FIG. 3. In this plot, the active vocabulary size is normalized so that 1 on the horizontal axis represents an active vocabulary consisting of all of the possible words. Similarly, the performance is normalized so that 1 on the vertical axis represents the theoretical perfect performance.

The second factor in the overall quality of a practical system is how completely the target machine can be controlled by spoken commands. The completeness of control is related directly to the size of the vocabulary of spoken commands provided. This relationship can be plotted as in FIG. 4. In this plot, the total vocabulary size is normalized so that 1 on the horizontal axis represents the size of the vocabulary thought to be ideal for the particular control application. Control is normalized so that 1 on the vertical axis represents the most complete control possible. Note that it may not be possible to design a vocabulary which will give perfectly complete control. There may always be some features that are not easily controlled by spoken commands.

A simple voice control system, such as the one illustrated above in reference to FIGS. 1A, 1B, uses what is known as a flat vocabulary in which the total vocabulary provided to control the machine is always active. From this it is clear that the two goals of maximizing the control of the machine and maximizing the speech recognition performance of the voice input module are diametrically opposed, since increasing the total vocabulary size to improve the control simultaneously decreases the performance. Conversely, any improvement in performance achieved by decreasing the size of the vocabulary comes at the expense of the control of the machine. This relationship is captured in the graph of FIG. 5.

There are a variety of ways to address these conflicting requirements to simultaneously maximize performance and control. One technique is to use a structured vocabulary in which the total vocabulary is divided into smaller sub-vocabularies. Different combinations of the sub-vocabularies may be active at any given time, but preferably at no time is the total vocabulary active. Therefore, the speech recognition performance of a system and the completeness of control over it are no longer functions of the same independent variable in that they can be optimized independently. Instead, the relationship between the size of the active vocabulary and the size of the total vocabulary can be related by Equation 1.

$$avs_n = kv_n \times tvs \qquad (1)$$

where:

$1 \leq n \leq N$;

N is the number of different active vocabularies possible in the total vocabulary;

$kv_n$ is the variable which relates the size of the $n^{th}$ active vocabulary to the size of the total vocabulary;

tvs is the size of the total vocabulary;

$avs_n$ is the size of the nth active vocabulary; and $0 < kv_n < 1$ for all n.

The relationship between the control of the target machine and recognition performance of the system that results from allowing the active vocabulary to be a subset of the total vocabulary can be captured in the graph of FIG. 6. By using a structured vocabulary defined in such a way that the size of any active vocabulary is always less than the size of the total vocabulary, both control and recognition performance of a complete system can be optimized. Note that the number of different active vocabularies will increase or decrease as necessary to achieve both the desired amount of control and performance.

However, the introduction of a structured vocabulary has complications. The active vocabulary defines which subset of commands can be spoken. This subset should preferably match the commands which the system is prepared to accept. If the two diverge, then the voice input module will be using an active vocabulary which does not contain the commands which are appropriate to control the system in its current state. With a structured vocabulary, the active vocabulary should match the state of the machine being controlled.

Voice Control System in which a Structured Vocabulary is used without directly determining the Actual State of the Ultrasound Machine.

The current design of voice control for medical ultrasound systems implements the simple model of voice control described above in which a flat vocabulary is used. All of the voice commands provided to control the machine are simultaneously active in the voice input module's vocabulary. Because of this limitation, the completeness of control over the ultrasound machine cannot be increased without suffering a degradation in recognition performance, as represented by FIG. 5 above.

It is possible to introduce a structured vocabulary in the current systems and thereby increase the completeness of control offered by spoken commands. However since the current designs are limited to a one-way communication link, there is no mechanism for the ultrasound system to communicate any changes to its state back to the voice input module. In order to guarantee that the state of the vocabulary matches the state of the system, the voice input module should be the only mode of machine control. No other mode of system control, such as the keyboard, can be active simultaneously with the voice input module. Such a design is diagrammed in FIG. 7, with FIG. 8 showing the control flow that is required in the voice input module. In reference to FIGS. 7 and 8, the voice input module changes the active vocabulary by selecting a subset of the total vocabulary in view of its knowledge of the state of the ultrasound machine: that is, what the machine is prepared to accept.

The limitation to controlling the ultrasound system by spoken commands alone is unacceptable for the majority of applications. It is preferable to be able to employ other methods of control in conjunction with the spoken commands.

Voice Control System in which a Structured Vocabulary is used in conjunction with directly determining the Actual State of the Ultrasound Machine.

With a two-way communication link between the voice input module and the ultrasound machine, a method can be designed for the ultrasound machine to communicate its state information back to the voice input module. This makes it possible to introduce a structured vocabulary into the speech recognition system that can track with the actual state of the ultrasound machine. In this manner, more complete control of the system can be provided without suffering a degradation in performance, while still allowing the use of the keyboard or other modes of machine control. The invention implementing this is described in the following figures and discussion.

Description of Elements in Invention Apparatus (FIGS. 9 and 9A)

The different elements of apparatus 20 in FIGS. 9 and 9A illustrating the invention are described below:

(22) *Microphone.* In one implementation, a Shure SM10 (Shure Brothers Inc., 222 Hartrey Avenue, Evanston, Ill. 60202-3696, Ph. 708-866-2200) headset microphone is used. However, any microphone suitable to speech recognition applications may be used. In addition, any mounting option may be used. For example, a lapel microphone, a hand-held microphone, or a stand-mounted microphone would all work. In addition, it would also be possible to design the system using a "far-talk" microphone, which is a microphone mounted on the equipment itself (computer or ultrasound machine) instead of a microphone attached to the operator in some manner.

(24) *Connection of microphone to speech recognition hardware.* In one implementation, a wired connection is used. However, any microphone connection may be used. One such example is a wireless connection using FM radio transmission.

(26) *Host computer.* In one implementation, an AT-class Personal Computer (PC) compatible computer is used. Note that a full computer is not required, as the operator does not need to interact with the computer monitor or keyboard. An embedded computer could be used, which would then be housed within the case of the ultrasound system. The choice of a type of computer depends on the choice of a speech recognition system. It may also be desirable to use a computer from Apple Computer of Cupertino, Calif., or another type such as a VME-based system or an STD-based system.

(28) *Connection of speech recognition system to host computer.* In one implementation, the speech recognition system is provided as an add-in card for an AT-class PC-compatible computer, and therefore the interface is accomplished using the ISA bus. However, other possibilities are that the speech recognition system may be a separate module connected via a serial interface, or it may be designed to interface to the bus of another type of host computer, such as a VME system, or an STD bus system.

(30) *Speech recognition hardware/software.* This consists of the hardware and software required to perform speech recognition. Any suitable commercial or custom speech recognition system may be used. In one implementation, an SIR20, purchased from Voice Control Systems (VCS, 14140 Midway Road, Suite 100, Dallas, Tex. 75244, Ph. 214-286-0300) was used. Other companies supply speech recognition products that would be suitable. Some possibilities include Vobot (Vobot Corporation, 5574 Everglades, Ventura, Calif. 93003, Ph. 805-339-9797), Voice Connexion (Voice Connexion, 17835 Skypark Circle, Suite C, Irvine, Calif. 92714, Ph. 714-261-2366), or Verbex (Verbex Voice Systems, Inc., 1090 King Georges Post Road, Building #107, Edison, N.J. 08837-3701, Ph. 908-225-5225).

(32) *Connection of host computer to ultrasound system.* In one embodiment, this is accomplished by an RS232 wired connection. Again, it is not limited to this. Other interfaces might be used, such as an RS422, or GPIB. Network connections may also be used, such as Ethernet or AppleTalk. Another approach that could be taken with an embedded design is for the host computer to use the computer bus of the ultrasound system.

(34) *Ultrasound system.* In one implementation, the system was an 128/XP from Acuson Corporation of Mountain View, Calif. Other ultrasound systems could be used, given the appropriate interface capability.

(36) *Keyboard.* System keyboard by which the operator typically controls the machine.

(38) *Foot-switch.* Foot-switch extension by which operator can have remote access to limited functions on the keyboard (typically two keys at a time).

Description of Elements in Functional Diagram of Invention (FIG. 10)

The operation of the apparatus 20 is illustrated by the functional diagram in FIG. 10, whose elements are described below:

(22') *Microphone input.* See description above in reference to FIGS. 9 and 9A or possibilities.

(42) *Signal processing.* This function is typically implemented as part of the commercial speech recognition product. In this case, it is part of the function of the SIR20 product.

(44) *Recognition engine.* This function is also part of the speech recognition product, both hardware and software. It compares the incoming speech to the active vocabulary of defined utterances to determine if the spoken word matches any of the defined commands.

(46) *Vocabulary.* The vocabulary contains all of the reference commands that can be spoken. The total vocabulary can be subdivided into groups, or sub-vocabularies, each of which may be selected or deselected as part of the active vocabulary. This function is also part of the speech recognition product, but it is customized to the particular application. Voice Control Systems provides the software tools to create the vocabulary, with the speech recognition engine using the active vocabulary to recognize the spoken commands. The vocabulary and sub-vocabularies may be stored on disk or in the host computer memory. Similar resources for the creation and management of vocabularies exist for the other commercial speech recognition products.

(48) *Executive.* The Executive is the program which interfaces between the ultrasound machine and the speech recognition system. It is a software module whose operation is described below in reference to FIGS. 11–13 and to the flowchart of FIG. 14 and is run on the host computer (26) identified in the diagram of FIG. 9. It implements the active vocabulary control, dynamic macros as described below, and the required state-tracking of the ultrasound machine. In a current implementation, this is run on a PC. It is possible that the host computer be another type of computer, or computing resources embedded within the ultrasound machine, as discussed above in reference to FIGS. 9 and 9A.

(50) *Connection of executive module to speech recognition engine.* The interface between the executive and the speech recognition engine depends on the choice of speech recognition system and host computer. In this case, it occurs over the ISA bus in the PC using the protocol established in the SIR20 Application Programmer's Interface (API). The SIR20 API is provided as part of the SIR20 product and is sufficient to allow someone of ordinary skill in the art of programming to implement the interface. Similar resources exist for the other commercial speech recognition products.

(52) *Connection of executive to the vocabulary.* The interface between the executive and the speech recognition vocabulary depends on the choice of speech recognition system and host computer. Typically it is part of the overall communication between the Executive and the speech recognition engine. In this case it occurs over the ISA bus in the PC using the protocol established in the SIR20 API. The fundamental capability is that the Executive be able to select which sub-vocabularies in the total vocabulary are active at any given time. This capability is provided by all of the vendors supplying speech recognition systems listed above in reference to FIGS. 9 and 9A.

(34) *Ultrasound system controller.* This is the software/hardware module that controls the overall ultrasound system, in this case the 128/XP.

(32) *Communication with ultrasound system.* The Executive has a bi-directional communication link with the ultrasound system. As described with FIGS. 9 and 9A, the physical link in this system is a RS232 connection. The interface supports both the Executive sending commands to the ultrasound machine, and the ultrasound machine reporting back changes in its state.

(36) *Ultrasound system keyboard.* The keyboard by which the operator typically controls the machine.

(38') *Other sources of control.* These might include, but are not limited to, a foot-switch, such as foot-switch 38 of FIG. 9, or an image-capture add-on, such as the Aegis product from Acuson corporation of Mountain View, Calif.

Operation of the Voice Control System of this Invention

In the preferred embodiment, sub-vocabularies are activated as a function of the actual state of the ultrasound system. In this manner, the user of the system is not limited only to voice control of the machine but may use multi-modal control, such as by means of a keyboard and/or foot-switch in addition to voice control. The state of the ultrasound machine can be altered by means of any one of the above-listed controls. If the state of the machine is such that a small sub-vocabulary is sufficient for adequate control of the ultrasound system, then recognition performance can be enhanced without compromising the completeness of control of the system. Active sub-vocabularies are therefore selected based on direct knowledge of the state of the ultrasound system. In the preferred embodiment, the state of the ultrasound system may be one or more of twelve different states of the Acuson 128/XP described below. Such states may be referred to as voice-command-determining states. When only verbal commands are used and recognized, as in the preferred embodiment, such states may be referred to as vocabulary-determining states. The number of possible states can be different from twelve depending on the ultrasound machine to be controlled and the vocabulary used to control it. The operation of the system of FIGS. 9, 9A and 10 will now be described by reference to the flow charts in FIGS. 11–14.

FIG. 11 is a state diagram of control flow in the Executive 48 of FIG. 10. As illustrated in FIG. 11, Executive 48 keeps track of the vocabulary-determining-states of the ultrasound machine in states B0 and B1. The Executive 48 either periodically interrogates the ultrasound system controller 34 to find out any changes in the ultrasound states, or alternatively, the ultrasound system controller 34 in FIG. 10 automatically periodically sends its vocabulary-determining-state or -states to the Executive 48. Thus, when the Executive determines that there has been a change in the vocabulary-determining-state or states of the ultrasound system, it selects the appropriate sub-vocabulary or sub-vocabularies to activate. The recognition engine 44 recognizes the voice command from signal processing 42 using the selected active sub-vocabulary or sub-vocabularies and the Executive translates such recognized command into a signal or signals that can control the ultrasound system.

The recognized voice command may be translated into keystroke codes that are recognized by the ultrasound system controller 34. Alternatively, the recognized voice commands may be translated into signals that are not codes of keystrokes of a keyboard in a manner known to those skilled in the art, where such signals are nevertheless recognizable by controller 34 for controlling the ultrasound system. The Executive 48 receives the recognized spoken commands from recognition engine 44 through line 50, translates the commands into a signal or signals, and sends such signal or signals to controller 34 through two-way communication link 32.

Description of Interrupt Service Routines

The process described above of receiving spoken voice commands and receiving changes in the state of the ultrasound system may both be handled by interrupts and interrupt service routines (ISR). The speech recognition engine asserts a hardware interrupt when it receives a new spoken voice command, and the ultrasound system with controller 34 asserts an interrupt when there is a change in the vocabulary-determining-state. The content of the interrupt service routines to handle these interrupts is illustrated in FIGS. 12 and 13. If hardware interrupts are deemed undesirable, the same functionality may be implemented by polling loops or other inter-processor messaging schemes. In the case of each interrupt service routine receiving an interrupt, the Executive 48 sets the appropriate flag. The "new spoken command" flag is set when the interrupt from the speech recognition engine 44 is received, and the "ultrasound state changed" flag is set when the interrupt from the ultrasound system controller 34 is received. After executing the interrupt service routines, the Executive then returns to the main program diagrammed in FIG. 14 and described below.

Description of Executive Program

FIG. 14 is a flow chart illustrating the operation of the Executive 48. The Executive checks the "ultrasound state changed" flag (block 100). If there is no change in state (diamond 102), the Executive returns to check the "new spoken command" flag (block 104). If the flag has not been set indicating that no new spoken voice command has been received (diamond 106), the Executive returns to block 100 to check the "ultrasound state changed" flag.

If the "new spoken command" flag has been set, the Executive fetches the spoken command from engine 44, and proceeds to block 108 to determine the required ultrasound commands, and sends such commands to the ultrasound system and clears the "new spoken command" flag (blocks 110, 112). Engine 44 performs the recognition of the spoken commands using the sub-vocabulary or sub-vocabularies active at the time and the Executive performs the translation of the spoken voice commands into the required ultrasound commands. The process of translating is described in a following section. The Executive then returns to block 100.

If there has been a change in the vocabulary-determining-state(s) of the ultrasound system, the "ultrasound state changed" flag will be set so that the Executive will proceed to block 120 to determine a new active sub-vocabulary or sub-vocabularies. The selected new sub-vocabulary or sub-vocabularies are then communicated to vocabulary 46 and recognition engine 44 (block 122) so that the engine will employ the new active sub-vocabulary or sub-vocabularies in the recognition of voice commands. The Executive then clears the "ultrasound state changed" flag (block 124) and returns to check the "new spoken command" flag.

Determination of New Ultrasound Vocabularies

The activation of sub-vocabularies must correspond to the overall actual state of the ultrasound machine. However, the only information necessary is that which directly determines the active sub-vocabulary or sub-vocabularies. Such information is referred to as the "vocabulary-determining-state." The vocabulary-determining-state information can be a subset of the total state information or state of the machine.

The information contained in the "vocabulary-determining-state" is dependent on how the vocabulary is designed. In the case of the vocabulary presented in the accompanying "Acuson Voice Interface on the 128/XP: Vocabulary Specification (English), Revision 0.4," attached hereto as Appendix I and made part of this application, the following information is retrieved from the ultrasound machine:

| Vocabulary-Determining-states: | |
|---|---|
| BMODE = | off/on |
| MMODE = | off/on |
| PW = | off/on |
| CW = | off/on |
| RES = | off/setup/on |
| CD = | off/setup/on |
| BCOLOR = | off/on |
| FREEZE = | off/on |
| CINE = | off/on |
| SPEECH = | off/on |
| TBALL = | off/on |
| SKEYS = | off/on |

Once these vocabulary-determining states of the machine are known, the logic used to set the correct active vocabulary is according to the pseudocode that follows. In many cases it is straightforward, as there may be a 1:1 mapping between the state of the machine and the various sub-vocabularies.

```
if(state of ultrasound machine has changed)
{
    de-activate all sub-vocabularies.
    if(BMODE==on)
    {
        activate sub-vocabulary BM.
    }
    if(MMODE==off)
    {
        activate sub-vocabulary MM1.
    }
    else
    {
        activate sub-vocabulary MM2.
    }
    if(PW==off)
    {
        activate sub-vocabulary PW1.
    }
    else
    {
        activate sub-vocabulary PW2.
    }
    if(CW==off)
    {
        activate sub-vocabulary CW1.
    }
    else
    {
        activate sub-vocabulary CW2.
    }
    if(RES==off)
    {
        activate sub-vocabulary RES1.
    }
    else if(RES==setup)
    {
        activate sub-vocabularies RES2 and
        RES3.
    }
    else
    {
        activate sub-vocabulary RES3.
    }
    if(CD==off)
    {
        activate sub-vocabulary CD1.
    }
    else if(CD==setup)
    {
        activate sub-vocabularies RES2 and
        CD2.
    }
    else
    {
        activate sub-vocabulary CD2.
    }
    if(CINE==off)
    {
        activate sub-vocabulary CINE1.
    }
    else
    {
        activate sub-vocabulary CINE2.
        de-activate all previously
        activated sub-vocabularies except
        CD2.
    }
    if(CINE==off)
    {
        if(FREEZE==off)
        {
            activate sub-vocabulary FR1.
        }
        else
        {
            activate sub-vocabulary FR2.
            de-activate other sub-
            vocabularies.
        }
    }
    if(BCOLOR==off)
    {
        activate sub-vocabulary BC1.
    }
    else
    {
        activate sub-vocabulary BC2.
    }
    if(TBALL==on)
    {
        activate sub-vocabulary TBALL.
    }
    else
    {
        de-activate sub-vocabulary TBALL.
    }
    if(SKEYS==on)
    {
        activate sub-vocabulary SKEYS.
    }
    else
    {
        de-activate sub-vocabulary SKEYS.
    }
    if(SPEECH==off)
    {
        activate sub-vocabulary SP.
        de-activate all other sub-
        vocabularies.
    }
}
```

The symbols listed above have the following meanings which are well known to those skilled in medical ultrasound technology. B-mode is the mode in which a 2-dimensional gray-scaled ultrasound image is displayed. M-mode displays the intensity of reflections along a sample line in the image over time. PW means that the ultrasound system is in the Pulse-Wave Doppler mode and CW means that the ultrasound system is in the Continuous-Wave Doppler mode.

RES means that a portion of the image is enlarged. CD is Color Doppler mode. BCOLOR means that the B-mode image is shown in color. FREEZE means that a particular frame is shown and frozen so that the current ultrasound data being acquired is not shown. CINE means that the recorded image for a set time period is being played back. SPEECH indicates whether the voice input module is on or off. TBALL indicates whether the trackball function is on or off. SKEYS indicates whether the soft keys of the 128/XP are on or off.

It is preferable that there be a one-to-one mapping between the vocabulary-determining-states and the sub-vocabularies as shown above, but it is not essential. More than one sub-vocabulary can correspond to one vocabulary-determining-state. In such cases, when the Executive determines the vocabulary-determining-state(s) of the ultrasound system, it renders active all the sub-vocabularies that correspond to such state(s). Similarly, each sub-vocabulary can correspond to more than one vocabulary-determining-state and be activated when the ultrasound system is in any one of such corresponding states.

The above-described preferred implementation requires that the speech recognition system support a total of 21 independent sub-vocabularies. The SIR20 system that has been used in the implementation supports only 16 independent sub-vocabularies. In order to implement this design with the SIR20, some of the independent sub-vocabularies must be combined.

To consolidate the vocabulary structure to have only 16 or fewer independent sub-vocabularies, the following changes can be made:

Eliminate sub-vocabularies BC1, BC2, FR1, FR2, TBALL and SKEYS. Make the voice commands that were formerly members of those sub-vocabularies members of all imaging mode sub-vocabularies (see definition of sub-vocabularies in the vocabulary listing).

The pseudocode for the routine to control the sub-vocabularies would have to be changed to what is listed below.

As illustrated by these changes in the assignment of voice commands to sub-vocabularies, the sub-vocabularies can be overlapping. A given voice command may be a member of more than one sub-vocabulary.

```
if(state of ultrasound machine has changed)
{
    de-activate all sub-vocabularies
    if(BMODE==on)
    {
        activate sub-vocabulary BM.
    }
    if(MMODE==off)
    {
        activate sub-vocabulary MM1.
    }
    else
    {
        activate sub-vocabulary MM2.
    }
    if(PW==off)
    {
        activate sub-vocabulary PW1.
    }
    else
    {
        activate sub-vocabulary PW2.
    }
    if(CW==off)
    {
        activate sub-vocabulary CW1.
    }
```

-continued

```
    }
    else
    {
        activate sub-vocabulary CW2.
    }
    if(RES==off)
    {
        activate sub-vocabulary RES1.
    }
    else if (RES==setup)
    {
        activate sub-vocabularies RES2 and
            RES3.
    }
    else
    {
        activate sub-vocabulary RES3.
    }
    if(CD==off)
    {
        activate sub-vocabulary CD1.
    }
    else if(CD==setup)
    {
        activate sub-vocabularies RES2 and
            CD2.
    }
    else
    {
        activate sub-vocabulary CD2.
    }
    if(CINE==off)
    {
        activate sub-vocabulary CINE1.
    }
    else
    {
        activate sub-vocabulary CINE2.
        de-activate all previously
            activated sub-vocabularies except
            CD2.
    }
    if(SPEECH==off)
    {
        activate sub-vocabulary SP.
        de-activate all other sub-
            vocabularies.
    }
}
```

Translation of Voice Commands to Ultrasound Commands

Implicit in this function is the interface between the voice input module and the ultrasound machine. This interface preferably has the following characteristics:

ability to send to the ultrasound machine all keystroke commands supported by the keyboard, ability for the ultrasound machine to return the "vocabulary-determining-state" described above, ability for the ultrasound machine to report which applications are receiving inputs (described further below).

With an interface offering such basic capability, the process of mapping spoken commands to ultrasound commands is a matter of determining which keystroke(s) must be sent. In most cases, for the vocabulary described, this is a one-to-one transformation. Note that the exact details of this mapping will depend on the particular ultrasound machine being controlled and the exact content of the vocabulary. As a particular example, the 128/XP keyboard provides a paddle switch labeled "Depth." This switch has three positions, down, centered, and up. To increase the scanning depth, this switch is pressed down. To decrease the scanning depth, this switch is pressed up. The vocabulary provides two commands for this control, "Deeper" and "Shallower." The command "Deeper" maps directly to a single depression down of the "Depth" paddle switch, and the command "Shallower" maps directly to a single depression up of the "Depth" paddle switch.

This process is completely analogous to assigning macros, in which each spoken command maps directly to a sequence of one or more keystrokes. With bi-directional communication, however, it is possible to design "dynamic macros." These are macros which can change depending on the state of the machine. Such macros are necessary if the spoken commands must implement functionality beyond what is directly contained in the interface between the voice input module and the ultrasound machine.

The vocabulary described contains such a command, "2D." This command must return the ultrasound machine to the default scanning state of B-mode only. In the case of the 128/XP, there is no single keystroke that implements this function. Instead, a sequence of keystrokes must be sent to disable all other scanning modes. For example, consider a situation in which the 128/XP has three different functions active in addition to the basic B-mode: M-mode, B-color and Cine. For this condition, the "vocabulary-determining-states" of the machine would be:

| | |
|---|---|
| BMODE = | on |
| MMODE = | on |
| PW = | off |
| CW = | off |
| RES = | off |
| CD = | off |
| BCOLOR = | on |
| FREEZE = | off |
| CINE = | on |
| SPEECH = | on |
| TBALL = | on |
| SKEYS = | on |

The spoken command "2D" must be translated to the sequence of commands "Cine off," "M-mode off" and "B-color off."

If, however, the 128/XP were in a different state, such as having only an M-mode image up, then the vocabulary-determining-states of the machine would be:

| | |
|---|---|
| BMODE = | off |
| MMODE = | on |
| PW = | off |
| CW = | off |
| RES = | off |
| CD = | off |
| BCOLOR = | off |
| FREEZE = | off |
| CINE = | off |
| SPEECH = | on |
| TBALL = | on |
| SKEYS = | off |

In this case, the spoken command "2D" must be translated to the single command "M-mode off." The soft keys (SKEYS) are inactive in this case because none of the active applications requires them.

This type of "dynamic macro," in which the commands to the ultrasound machine corresponding to a particular spoken command vary depending on the state or states of the ultrasound machine, can only be implemented because the Executive has knowledge of the state(s) of the ultrasound machine. Dynamic macros such as this can be readily implemented for other commands. Thus, if the desired state of the ultrasound system is known as indicated by the spoken voice command, and the starting actual state of the system is also determined by or otherwise known to the Executive, then a similar process like the one above for "2-D" can be performed to derive from the actual and desired states the signal or signals that will cause the ultrasound system to be in the desired state. The term "state" as used in the preceding sentence, includes the "vocabulary-determining states," but is not limited thereby.

A second type of "dynamic macro" is required when the machine must first be put into a particular state in order to receive the desired inputs. Since more than a single application can be active on the 128/XP at a particular time, the input resources have to be directed to one of the many possible applications. If the 128/XP is not directing the inputs to the application which is to receive the next command, then the state of the 128/XP must be changed to direct the inputs correctly.

For the Executive to have enough information to implement this type of "dynamic macro," it must be able to obtain the status of where various inputs will be directed: that is, what application will receive each input. This can be represented as a chart detailing all the supported inputs and which applications are receiving the input. If an application is active on the 128/XP, but it is not receiving inputs, the method on the 128/XP for making it receive inputs is to send the keycode for that application. For example, consider a situation on the 128/XP in which CINE has been invoked and put into the frozen state (i.e., the image is still), and then CALCs has been invoked (CALC is a function in which left and right calipers are used to enable users to measure an image on the screen). Within CALCs, a CALIPER has been requested to take the measurements. For this situation, the input allocation would be as follows:

| Input Mode | Owner Function |
|---|---|
| Trackball | CALIPER |
| Softkeys | CALIPER |
| Alpha Keyboard | off |

If the operator now wishes to cause CINE to enter REVIEW (REVIEW is a function in which the image frames recorded for a set time period of ultrasound imaging are re-played in a loop), the spoken command is "review." In order to start the REVIEW function in CINE, the CINE application must first be set to receive inputs. The spoken command must therefore be translated into two keystrokes:

send the CINE keystroke (to make the application receive the inputs).

send the REVIEW keystroke.

In other words, the 128/XP would respond to the CINE keystroke by first changing the input allocation of "Trackball" and "Softkeys" to "CINE" in the above table, and then respond to the REVIEW keystroke. If, however, CALCs had not been invoked and CINE had been invoked by itself, then the spoken command "review" would be translated into a single keystroke:

send the REVIEW keystroke.

This second type of "dynamic macro," in which the ultrasound machine must first be put into a state to receive the desired command, can only be implemented because the Executive has bi-directional communication with the ultrasound machine and can retrieve this information on how the input will be interpreted.

The exact details for this type of dynamic macro will be different for each command, and some commands may not even require it. However, for those commands that do require it, the general program would be structured as described below. As will be evident to those skilled in the art, the "dynamic macro" feature may be used in conjunction with the structured vocabulary feature described above to further enhance performance.

```
if(command to be sent requires dynamic macro)
{
    check status of input resources on
    128/XP.
    if(target application is not receiving
    inputs)
    {
        send keycode for target application.
    }
    send command.
}
```

Vocabulary Listing

The vocabulary consists of all of the commands which the operator is allowed to speak. The total vocabulary is divided into multiple sub-vocabularies. Each command may have membership in one or more of the sub-vocabularies. There is no limit to the number of words which may be in any sub-vocabulary or the entire vocabulary, except as imposed by the constraints of the particular speech recognition system being used.

The vocabulary for the 128/XP is split into the sub-vocabularies listed below, which are identified by their application to the ultrasound machine. It is noted that for some vocabulary-determining-states of the ultrasound system, each of such states corresponds to more than one sub-vocabulary. However, not all of such corresponding sub-vocabularies are rendered to be active at the same time in the speech recognition process, as illustrated in the pseudocodes above. For example, the vocabulary-determining-state RES corresponds to three sub-vocabularies RES1, RES2, RES3, but not all three sub-vocabularies are made active simultaneously. If the RES mode is active, there is no need to attempt to recognize the voice command "RES_ON," while there is need to recognize the command "RES_OFF". In such event, RES1 is de-activated and RES3 is activated. In general, at most only one of the two sub-vocabularies RES1, RES3 would be active at any time. To enhance recognition performance, similar sounding commands are placed into different sub-vocabularies, as in the case of "RES_ON" and "RES_OFF". Since the two sub-vocabularies would not be active simultaneously, as illustrated in the example, this reduces the chances for errors in recognition. Recognition performance is also enhanced by this feature because it reduces the size of sub-vocabularies. In general, a command for turning on a vocabulary-determining-state of the ultrasound system and having the word "on" and another command for turning off such vocabulary-determining-state and having the word "off" are in different sub-vocabularies.

| Sub-Vocabularies to Control Major Imaging Modes | Description |
| --- | --- |
| BM | Commands to control B-mode. |
| RES1 | Commands to control RES mode. |
| RES2 | |
| RES3 | |

| Sub-Vocabularies to Control Major Imaging Modes | Description |
| --- | --- |
| CD1 | Commands to control |
| CD2 | Color Doppler mode. |
| MM1 | Commands to control |
| MM2 | M-mode. |
| PW1 | Commands to control |
| PW2 | PW Doppler mode. |
| CW1 | Commands to control |
| CW2 | CW Doppler mode. |

| Sub-Vocabularies to Control Image Display Functions | Description |
| --- | --- |
| BC1 | Commands to control the |
| BC2 | B-color function |
| FR1 | Commands to control the |
| FR2 | Freeze function |
| CINE1 | Commands to control the |
| CINE2 | CINE function |

| Sub-Vocabularies to Control Input Methods | Description |
| --- | --- |
| TBALL | Commands to control the trackball |
| SKEYS | Commands to control the softkeys |
| SP | Commands to activate or de-activate the speech interface |

All of the commands in the total vocabulary are defined in the following table:

| Command | Sub-Vocabulary Membership | Action |
| --- | --- | --- |
| 2D | All sub-vocabularies except SP. | Returns machine to B-mode only display. |
| Print | All sub-vocabularies except SP. | Captures the image to hardcopy printer. |
| Record | All sub-vocabularies except SP. | Begins VCR recording. |
| Stop_Recording | All sub-vocabularies except SP. | Stops VCR recording. |
| Left_Caliper | All sub-vocabularies except SP. | Engages the left caliper, or activates it. |
| Left_Caliper_Off | All sub-vocabularies except SP. | Disengages the left caliper. |
| Right_Caliper | All sub-vocabularies except SP. | Engages the right caliper, or activates it. |
| Right_Caliper_Off | All sub-vocabularies except SP. | Disengages the right caliper. |
| Trace | All sub-vocabularies except SP. | Engages the trace function. |
| Trace_Off | All sub-vocabularies except SP. | Disengages trace. |
| Deactivate | All sub-vocabularies except SP. | Disengages speech recognition (puts it in standby until receiving the "Active" command). |
| Transducer_Switch | All sub-vocabularies for major imaging modes | Switches between left and right transducer. |
| Multi-Hertz | All sub-vocabularies for major imaging | Cycles through the imaging frequencies |

| Command | Sub-Vocabulary Membership | Action |
| --- | --- | --- |
| | modes | suported by the probe. |
| Flip | BM | Flips the B-mode image display (right to left). |
| Invert | BM | Inverts the B-mode image display. |
| Cursor | BM | Activates or deactivates the cursor. |
| Deeper | BM,MM2 | Increases the scanning depth. |
| Shallower | BM,MM2 | Decreases the scanning depth |
| Transmit_Up | BM,MM2 | Moves focus up. Cycles through focal zone options. |
| Transmit_Down | BM,MM2 | Moves focus down. Cycles through focal zone options. |
| M_Mode_On | MM1 | Engages M-mode. |
| M_Mode_Off | MM2 | Disengages M-mode. |
| Pulsed_Doppler_On | PW1 | Engages Pulsed Doppler Mode. |
| Pulsed_Doppler_Off | PW2 | Disengages Pulsed Doppler Mode. |
| CW_On | CW1 | Engages Continuous Wave Doppler Mode. |
| Update | CW2 | Forces B-mode Updates when in Update mode CW. |
| CW_Off | CW2 | Disengages Continuous Wave Doppler Mode. |
| Doppler_Invert | CW2,PW2 | Inverts the Doppler strip. |
| Scale_Up | CW2,PW2 | Compresses the scale on the Doppler strip. |
| Scale_Down | CW2,PW2 | Expands the scale on the Doppler strip. |
| Baseline_Up | CW2,PW2 | Moves the baseline up in the Doppler strip display. |
| Baseline_Down | CW2,PW2 | Moves the baseline down in the Doppler strip display. |
| Increment_Gate | CW2,PW2 | Increments the size of the Doppler gate. |
| Decrement_Gate | CW2,PW2 | Decrements the size of the Doppler gate |
| Sweep_Faster | MM2,CW2,PW2 | Accelerates the M-mode or Doppler sweep rate. |
| Sweep_Slower | MM2,CW2,PW2 | Decelerates the M-mode or Doppler sweep rate. |
| Full_Screen_On | MM2,CW2,PW2 | Displays the strip in full-screen. |
| Full-Screen_Off | MM2,CW2,PW2 | Returns the strip to normal ⅓–⅔ display. |
| RES-On | RES1 | Engages RES mode. |
| Position | RES2 | Switches RES control to position. |
| Size | RES2 | Switches RES control to size. |
| RES_Off | RES3 | Disengages RES mode. |
| Color_Doppler_On | CD1 | Engages the Color Doppler Mode |
| Color_Doppler_Off | CD2 | Disengages the Color Doppler Mode. |
| Freeze | FR1 | Freezes scanning. |
| Unfreeze | FR2 | Unfreezes scanning. |
| B_Color_On | BC1 | Engages Bcolor Mode. |
| B_Color_Off | BC2 | Disengages B-Color Mode. |
| Cine_On | CINE1 | Engages Cine Mode. |
| Review | CINE2 | Puts Cine into review. |
| Stop | CINE2 | Stops Cine Review. |
| Cine_Off | CINE2 | Disengages Cine Mode. |
| Key_1 | SKEYS | Selects the first soft-key (leftmost). |
| Key_2 | SKEYS | Selects the second soft-key. |
| Key_3 | SKEYS | Selects the third soft-key. |
| Key_4 | SKEYS | Selects the fourth soft-key (rightmost). |
| Track_Right | TBALL | Slews the trackball to the right. |
| Track_Left | TBALL | Slews the trackball to the left. |
| Track_Up | TBALL | Slews the trackball up. |
| Track_Down | TBALL | Slews the trackball down. |
| Activate | SP | Engages speech recognition. |

While the invention has been described above by reference to various embodiments, other approaches employing the same principles may be adopted. For example, while the signal processing, vocabulary and recognition engine may be implemented using the SIR 20 from Voice Control Systems, such functions may also be implemented using the design set forth in Appendices 2 and 3 attached hereto and made part of this application. Such and other changes and modifications may be made without departing from the scope of the invention which is to be limited only by the appended claims. The Appendices 1, 2 and 3 are listed below:

(1) Acuson Voice Interface on the 128/XP: Vocabulary Specification (English);

(2) Acuson Voice Interface on the 128/XP: Core Functional Specification; and (3) Acuson Voice Interface on the 128/XP: Subsystem Architecture Requirements.

APPENDIX 1

ACUSON VOICE INTERFACE

ON THE 128/XP:

VOCABULARY SPECIFICATION

(ENGLISH)

*REVISION 0.4*

February 24, 1995

Responsible Engineer

Dan Need

ACUSON CONFIDENTIAL

1. Table of Contents

1. TABLE OF CONTENTS   2

2. SCOPE   3

3. REVISION HISTORY   3

4. APPLICABLE DOCUMENTS   3

5. OVERVIEW   3

6. VOCABULARY LISTING   4

AVI XP Vocabulary Specification

ACUSON CONFIDENTIAL

2. Scope

This document describes the particulars of the vocabulary supported by the Acuson Voice Interface, as implemented on the 128 and XP. This specifies the English vocabulary. Other languages will implement the same capability with different spoken commands assigned to them.

3. Revision History

| Revision | Date | Description |
| --- | --- | --- |
| 0.1 | 12/06/94 | First preliminary draft. |
| 0.2 | 02/03/95 | Revised sub-vocabulary distribution. |
| 0.3 | 2/16/95 | Revised sub-vocabulary distribution. |
| 0.4 | 2/24/95 | Corrected description of "Print". |

4. Applicable Documents

An overview of the entire Acuson Voice Interface subsystem, as implemented on the XP and 128 in provided in:

- Acuson Voice Interface on the 128/XP: Subsystem Architecture Requirements.

The following documents describe in more detail the other components of the subsystem:

- Acuson Voice Interface on the 128/XP: Core Functional Specification.
- Acuson Voice Interface on the 128/XP: Executive Functional Specification *(not complete)*.
- Acuson Voice Interface on the 128/XP: Core/Executive Interface Specification.

5. Overview

The Acuson Voice Interface is a speaker-dependent system, and each operator must train it to their own voice. However the primary vocabulary is still defined by Acuson. This includes both the utterances which the operators are expected to use, and the actions which will result on the system. No mechanism exists to force the operator to speak the command as specified, but it is assumed that they will cooperate. To encourage this cooperation, the vocabulary is designed to be intuitive.

The vocabulary consists of all of the commands which the operator is allowed to speak. The total vocabulary is divided into multiple sub-vocabularies. Each command may have membership in one or more of the sub-vocabularies. There is no limit to the number of words which may be in any sub-vocabulary or the entire vocabulary, except as imposed by the amount of memory available (see the ACUSON VOICE INTERFACE ON THE 128/XP: CORE FUNCTIONAL SPECIFICATION).

The total number of sub-vocabularies must be less than 32, an arbitrary limitation imposed by the design of the data structures on the core (see the ACUSON VOICE INTERFACE ON THE 128/XP: CORE FUNCTIONAL SPECIFICATION). The sub-vocabularies can be enabled or disabled in any combination.

The utterance for each command must be less than 2 seconds in length. Each utterance may consist of multiple words, but they must expressed as a connected utterance.

Ultimately, it may be desirable to support user-defined macros. That capability is not included in this iteration of the product.

AVI XP Vocabulary Specification

ACUSON CONFIDENTIAL

6. Vocabulary Listing

This vocabulary is split into the following sub-vocabularies. The sub-vocabularies are separated by their application to the ultrasound machine.

| Sub-Vocabularies to Control Major Imaging Modes | Description |
|---|---|
| BM | Commands to control B-mode. |
| RES1 | Commands to control RES mode. |
| RES2 | |
| RES3 | |
| CD1 | Commands to control Color Doppler mode. |
| CD2 | |
| MM1 | Commands to control M-mode. |
| MM2 | |
| PW1 | Commands to control PW Doppler mode. |
| PW2 | |
| CW1 | Commands to control CW Doppler mode. |
| CW2 | |

| Sub-Vocabularies to Control Image Display Functions | Description |
|---|---|
| BC1 | Commands to control the B-Color function |
| BC2 | |
| FR1 | Commands to control the Freeze function. |
| FR2 | |
| CINE1 | Commands to control the CINE function. |
| CINE2 | |

AVI XP Vocabulary Specification

ACUSON CONFIDENTIAL

| Sub-Vocabularies to Control Input Methods | Description |
|---|---|
| TBALL | Commands to control the trackball. |
| SKEYS | Commands to control the softkeys. |
| SP | Commands to control the speech interface. |

All of the commands in the total vocabulary are defined in the following table:

| Command | Sub-Vocabulary Membership | Action |
|---|---|---|
| 2D | All sub-vocabularies except SP. | Returns machine to B-mode only display. |
| Print | All sub-vocabularies except SP. | Captures the image to the hardcopy printer attached to system. |
| Record | All sub-vocabularies except SP. | Begins VCR recording (if VCR is installed). |
| Stop_Recording | All sub-vocabularies except SP. | Stops VCR recording |
| Left_Caliper | All sub-vocabularies except SP. | Engages the left caliper, or activates it. |
| Left_Caliper_Off | All sub-vocabularies except SP. | Disengages the left caliper. |
| Right_Caliper | All sub-vocabularies except SP. | Engages the right caliper, or activates it. |
| Right_Caliper_Off | All sub-vocabularies except SP. | Disengages the right caliper. |
| Trace | All sub-vocabularies except SP. | Engages the trace function. |
| Trace_Off | All sub-vocabularies except SP. | Disengages trace. |
| Deactivate | All sub-vocabularies except SP. | Disengages speech recognition. (Puts it in standby until receiving the "Activate" command.) |
| Transducer_Switch | All sub-vocabularies for major imaging modes. | Switches between left and right transducer. |
| Multi_Hertz | All sub-vocabularies for major imaging modes. | Cycles through the imaging frequencies supported by the probe. |
| Flip | BM | Flips the B-mode image display (right to left). |

AVI XP Vocabulary Specification

ACUSON CONFIDENTIAL

| Command | Sub-Vocabulary Membership | Action |
|---|---|---|
| Invert | BM | Inverts the B-mode image display. |
| Cursor | BM | Activates or deactivates the cursor. |
| Deeper | BM,MM2 | Increases the scanning depth. |
| Shallower | BM,MM2 | Decreases the scanning depth. |
| Transmit_Up | BM,MM2 | Moves focus up. Cycles through focal zone options. |
| Transmit_Down | BM,MM2 | Moves focus down. Cycles through focal zone options. |
| M_Mode_On | MM1 | Engages M-Mode |
| M_Mode_Off | MM2 | Disengages M-mode. |
| Pulsed_Doppler_On | PW1 | Engages Pulsed Doppler Mode. |
| Pulsed_Doppler_Off | PW2 | Disengages Pulsed Doppler Mode. |
| CW_On | CW1 | Engages Continuous Wave Doppler Mode. |
| Update | CW2 | Forces B-Mode updates when in Update mode CW. |
| CW_Off | CW2 | Disengages Continuous Wave Doppler Mode. |
| Doppler_Invert | CW2,PW2 | Inverts the Doppler strip. |
| Scale_Up | CW2,PW2 | Compresses the scale on the Doppler strip. |
| Scale_Down | CW2,PW2 | Expands the scale on the Doppler strip. |
| Baseline_Up | CW2,PW2 | Moves the baseline up in the Doppler strip display. |
| Baseline_Down | CW2,PW2 | Moves the baseline down in the Doppler strip display. |
| Increment_Gate | CW2,PW2 | Increments the size of the Doppler gate |
| Decrement_Gate | CW2,PW2 | Decrements the size of the Doppler gate |
| Sweep_Faster | MM2,CW2,PW2 | Accelerates the M-Mode or Doppler sweep rate. |
| Sweep_Slower | MM2,CW2,PW2 | Decelerates the M-Mode or Doppler sweep rate. |
| Full_Screen_On | MM2,CW2,PW2 | Displays the strip in full-screen. |
| Full_Screen_Off | MM2,CW2,PW2 | Returns the strip to normal 1/3-2/3 display. |
| RES_On | RES1 | Engages RES mode. |
| Position | RES2 | Switches RES control to position. |
| Size | RES2 | Switches RES control to size. |

AVI XP Vocabulary Specification

ACUSON CONFIDENTIAL

| Command | Sub-Vocabulary Membership | Action |
|---|---|---|
| RES_Off | RES3 | Disengages RES mode. |
| Color_Doppler_On | CD1 | Engages the Color Dopple Mode |
| Color_Doppler_Off | CD2 | Disengages the Color Doppler Mode. |
| Freeze | FR1 | Freezes scanning. |
| Unfreeze | FR2 | Unfreezes scanning. |
| B_Color_On | BC1 | Engages B-Color Mode. |
| B_Color_Off | BC2 | Disengages B-Color Mode. |
| Cine_On | CINE1 | Engages Cine Mode. |
| Reveiw | CINE2 | Puts Cine into review. |
| Stop | CINE2 | Stops Cine review. |
| Cine_Off | CINE2 | Disengages Cine Mode. |
| Key_1 | SKEYS | Selects the first soft-key (left-most). |
| Key_2 | SKEYS | Selects the second soft-key. |
| Key_3 | SKEYS | Selects the third soft-key. |
| Key_4 | SKEYS | Selects the fourth soft-key (right-most). |
| Track_Right | TBALL | Skews the trackball to the right. |
| Track_Left | TBALL | Skews the trackball to the left. |
| Track_Up | TBALL | Skews the trackball up. |
| Track_Down | TBALL | Skews the trackball down. |
| Activate | SP | Engages speech recognition. |

AVI XP Vocabulary Specification

ACUSON CONFIDENTIAL

APPENDIX 2

ACUSON VOICE INTERFACE

ON THE 128/XP:

CORE FUNCTIONAL SPECIFICATION

*REVISION 1:1*

February 24, 1995

Responsible Engineer

Dan Need

AVI XP Core Functional Specificaton

ACUSON CONFIDENTIAL

1. Table of Contents

| | |
|---|---|
| 1. TABLE OF CONTENTS | 2 |
| 2. SCOPE | 3 |
| 3. REVISION HISTORY | 4 |
| 4. APPLICABLE DOCUMENTS | 4 |
| 5. FUNCTIONAL OVERVIEW | 4 |
| 6. FUNCTIONAL REQUIREMENTS | 4 |
|    6.1 ENGLISH LANGUAGE | 4 |
|    6.2 SPEAKER-DEPENDENT | 4 |
|    6.3 DISCRETE UTTERANCE | 5 |
|    6.4 VOCABULARY | 5 |
|    6.5 RESPONSE SPEED | 5 |
|    6.6 RAW RECOGNITION RATE | 5 |
| 7. SOFTWARE | 5 |
|    7.1 FUNCTIONAL OVERVIEW | 5 |
|    7.2 CORE/EXECUTIVE COMMUNICATION | 6 |
|       7.2.1 PROTOCOL | 6 |
|       7.2.2 EXECUTIVE TO CORE MESSAGES | 6 |
|       7.2.3 CORE TO EXECUTIVE MESSAGES | 7 |
|    7.3 DATA STRUCTURES | 8 |
|       7.3.1 WORD STRUCTURE | 8 |
| 8. HARDWARE REQUIREMENTS | 8 |
|    8.1 ANALOG INPUT | 9 |
|    8.2 ANALOG TO DIGITAL CONVERSION | 9 |
|    8.3 INPUT GAIN | 9 |

AVI XP Core Functional Specificaton

| | |
|---|---|
| 8.4 DSP | 9 |
| 8.5 RAM | 9 |
| 8.6 ROM | 9 |
| 8.7 DUAL PORT RAM | 9 |
| 8.8 INTERPROCESSOR SYNCHRONIZATION | 10 |

9. ENHANCEMENTS                                                                          10

| | |
|---|---|
| 9.1 NOISE CANCELLATION | 10 |
| 9.2 POST-PROCESSING | 10 |
| 9.3 AUDIO OUTPUT | 10 |

ACUSON CONFIDENTIAL

2. Scope

This document describes the requirements on the Core Module for the Acuson Voice Interface. The requirements include the necessary performance, the software interface to the Executive Module, and the hardware platform for the Core.

3. Revision History

| Revision | Date | Description |
|---|---|---|
| 0.1 | 11/21/94 | First preliminary draft. |
| 1.0 | 12/05/94 | Draft submitted to UUJ for project quotation. |
| 1.1 | 2/24/95 | Corrects document cross-references. |

4. Applicable Documents

An overview of the entire Acuson Voice Interface subsystem, as implemented on the XP and 128 in provided in:

- Acuson Voice Interface on the 128/XP: Subsystem Architecture Requirements

The following documents describe in more detail the other components of the subsystem:

- Acuson Voice Interface on the 128/XP: Executive Functional Specification *(note complete)*
- Acuson Voice Interface on the 128/XP: Core/Executive Interface Specification
- Acuson Voice Interface on the 128/XP: Vocabulary Specification

5. Functional Overview

The Core Module provides the fundamental speech recognition for the Acuson Voice Interface. It includes the algorithms which execute the automatic speech recognition, as well as the hardware platform on which the algorithms run. The Core executes the speech recognition under control of the Executive, which then takes the appropriate actions to control the ultrasound machine.

6. Functional Requirements

The following requirements represent the high-level performance that must be provided by the Core.

6.1 Multiple Language

The initial design of the Core is for the English and German languages. The basic capabilities, however, must not preclude migration to other languages.

6.2 Speaker-Dependent

The basic technology is speaker dependent. The system must be trained to the voice of each user. Capabilities that must be supported for training are:
- train a previously untrained command.
- refresh the training of a previously trained command.
- remove the training of a previously trained command.

The system must adequately train to the operators voice in less than 5 repetitions of each command.

AVI XP Core Functional Specificaton

ACUSON CONFIDENTIAL

Although the initial product design is speaker-dependent, it is the intent for this Core to support migration to a form of speaker-independence. This will be based on the creation of templates that represent a speaker-independent sampling of the operator population, so the underlying Core algorithms will be the same for speaker-dependent or independent operation. The Executive module will manage the creation of the speaker-independent templates, and any of the additional decision making required.

6.3 Discrete Utterance

The Core must recognize discretely uttered commands. These can be of length up to 2 seconds and may consist of multiple connected words.

6.4 Vocabulary

The total vocabulary must only be limited in size by the amount of storage available. Selectable subvocabularies of the total vocabulary can be active at any particular time. The speech recognition on the incoming utterance will only be performed against the active subset. The total size of an active subvocabulary is also unlimited, except by hardware.

As the number of words in the active subvocabulary grows, the response time and recognition performance can be expected to degrade. See Section 6.7, Measure of Performance, for details on how the performance will be measured.

6.5 Response Speed

The latency between the end of a spoken utterance and the completion of the recognition, as defined by the passing of the token of the recognized word back to the Executive, must be less than 100msec.

6.6 Raw Recognition Rate

The Core must provide a raw recognition rate of at least 98%, as specified in Section 6.7, Measure of Performance.

6.7 Measure of Performance

The performance of the system will be measured quantitatively for its raw recognition rate. It will be tested by using the English Language vocabulary. The vocabulary will be provided in 5 different speakers. The system is trained the required number of times, as determined by the system design. Then it is tested for raw recognition rate on the vocabulary for each speaker.

7. Software

The Core is designed to execute the speech recognition under the control of the Executive. The communication between the Executive and the Core is accomplished by means of a dual-port RAM, with semaphores to simplify software handshaking for the inter-processor synchronization.

7.1 Functional Overview

The capabilities of the hardware and the interface described in this document are designed to support a speech recognition algorithm based on Template Matching with Dynamic Time Warping. The basic approach is diagrammed below. While the implementation details of the automatic speech recognition technology are not important to this specification, this block diagram provides a context in which to understand the other requirements.

AVI XP Core Functional Specificaton

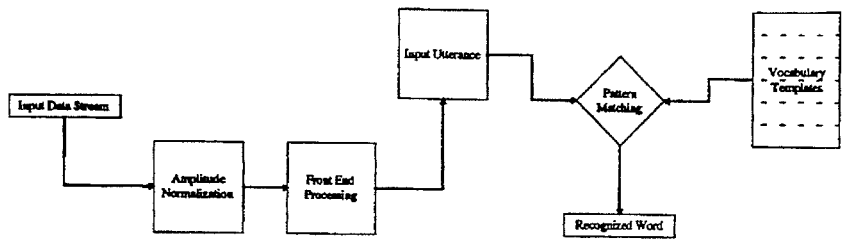

Figure 1: Core Software Diagram

The Core provides a dedicated speech recognition engine. It performs the recognition on the incoming speech under the supervisory control of the Executive. In general, the incoming data stream is searched to locate discrete utterances. The isolated utterances are processed and compared to the templates stored as the vocabulary. The input utterance is always matched against the currently active subset of the vocabulary.

The complete vocabulary is split into an active subvocabulary and inactive subvocabulary by the use of the VOCABULARY_IDENTIFIER in each word and the VOCABULARY_MASK. The VOCABULARY_MASK is and-ed with the VOCABULARY_IDENTIFIER in each word. If the result is non-zero, then the word is identified as part of the active subvocabulary and included in the pattern matching search. If not, then the word is excluded from the current search.

7.2 Core/Executive Communication

The communication that will eventually be defined here will detail the specific protocols to be followed and the messages that are supported. Currently, the protocol is undefined. The messages called out are not an exhaustive list but serve to identify the capability that must be supported in the final version.

7.2.1 Protocol

The protocol must support the passing of the individual commands listed out below, as well as data such as the word data structure.

*(This needs to be defined.)*

7.2.2 Executive to Core Messages

These messages allow the Executive to control the recognition process on the Core.

7.2.2.1 Set Mode

Sets the mode to either:
- train
- recognize
- idle

In the event that the mode is set to train, an argument is included to indicate the WORD_IDENTIFIER for the word to be trained. The Core should detect a spoken utterance and merge it with the existing template for the designated word. Upon completion of the training process, the Core should return the TRAINING_ACKNOWLEGMENT message indicating success or failure of the training pass.

AVI XP Core Functional Specificaton

ACUSON CONFIDENTIAL

When the mode is set to recognize, an argument is included to indicate the active VOCABULARY_MASK. The Core should search the incoming data stream to detect spoken commands. The module should return the RECOGNITION_ACKNOWLEGMENT message to indicate the success or failure of the recognition process.

7.2.2.2 Flush_Template

This includes an argument to indicate the WORD_IDENTIFIER of the template to be flushed. Flushing a template resets the TRAINING_COUNT to 0. This has the effect of completely untraining a word.

7.2.2.3 Put_Template

Transfers a WORD_STRUCTURE from the Executive to the Core.

7.2.2.4 Get_Template

Requests that the Core provide a WORD_STRUCTURE. The WORD_IDENTIFIER of the word to be transferred is provided in the argument.

7.2.2.5 Set_Input_Gain

Instructs the Core to set the input gain to the value included in the argument.

7.2.2.6 Abort

Instructs the Core to abort its current activity, which may be training or recognition.

7.2.3 Core to Executive Messages

7.2.3.1 Recognition_Success

Indicates to the Executive that a valid word has been recognized. The five words which best match the spoken utterance are reported. The WORD_IDENTIFIER of each of the words, as well as a measure of the closeness of the pattern to the input utterance, are returned as the argument.

7.2.3.2 Recognition_Failure

Indicates to the Executive that some failure in the recognition process has occurred. The failure mode is indicated in the argument. The possible modes are:
- too_loud: the input stream is too loud, so it is causing clipping on the analog to digital conversion.
- too_quiet: the input stream is too quiet, so sufficient dynamic range is not provided.
- too_close: the input stream does not clearly match a single template, but is close to more than one. Also returns the WORD_IDENTIFIER of the five best matches, together with the measure of closeness for each.

7.2.3.3 Training_Success

Indicates to the Executive that the training pass has been successfully completed.

7.2.3.4 Training_Failure

Indicates to the Executive that the training pass has failed. The failure mode is indicated in the argument to this message. The possible modes are:

AVI XP Core Functional Specificaton

ACUSON CONFIDENTIAL

- too_loud: the input stream is too loud, so it is causing clipping on the analog to digital conversion.
- too_quiet: the input stream is too quiet, so sufficient dynamic range is not provided.
- too_distant: the input stream represents a pattern that is deemed to be so disimilar to the existing template that it must not belong to the same utterance. Training is rejected in this case as the resulting aggregated template would not provide good performance for either the original utterance or the new one.

7.2.3.5 Template Passing Complete

This message is passed in response to a PUT_TEMPLATE or GET_TEMPLATE from the Executive. It indicates to that the Core has successfully either loaded up the requested template, or removed the template from the dual-port RAM.

7.3 Data Structures

The Core Module interacts with the Executive Module on the basis of the WORD_STRUCTURE. Logically, these are combined to form a representation of the entire vocabulary, as spoken by a particular voice, but the Core has no knowledge of anything but the basic words.

7.3.1 Word Structure

The basic element of the vocabulary is the word. This is represented by a data structure, known here as the WORD_STRUCTURE. It contains all of the information necessary for the Core to perform speech recognition. The structure is defined to support words of varying length, although the structure itself is padded out to a fixed length that allows a maximum utterance of 2 seconds.

The representation of an utterance is based on a 10msec frame rate. Each frame is represented by vector that may include up to 20 elements, each of word (2 bytes) length. To support a maximum word length of 2 seconds, the fixed length of the structure is 4KBytes. This is based on the storage need of the template itself, rounded out to support the overhead:

$$2\,sec/word \times 100\,frames/sec \times 20\,bytes/frame = 4000\,bytes/word$$

The elements of this structure are:
- WORD_IDENTIFIER: 2 byte number providing a unique identificaion of the word.
- VOCABULARY_IDENTIFIER: 2 byte mask to indicate whether this word should be included as an active member of the vocabulary being searched.
- TRAINING_COUNT: 2 byte number to record the number of training interations which have been used to create the template.
- TEMPLATE_LENGTH: 2 byte number indicating the length of the template, in frames.
- TEMPLATE[ ]: array of vectors to represent the word. One vector corresponds to a single frame in the utterance.

8. Hardware Requirements

The hardware platform for the Core is diagrammed in the figure below. It provides a generic signal processing platform suitable for speech processing. The platform is designed to be slaved to a host, the Executive. The two can interface by either dual-port RAM or interrupts.

ACUSON CONFIDENTIAL

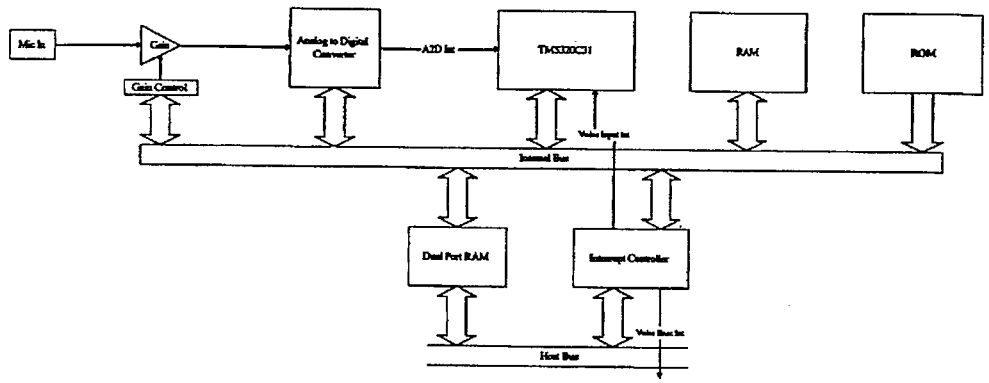

Figure 2: Core Hardware Diagram

8.1 Analog Input

The core hardware must accept a single channel of analog input. The maximum input voltage is ...

*(What is the maximum input voltage from these microphones?).*

8.2 Analog to Digital Conversion

The analog input is sampled at 12KHz to 16 bit resolution. The input anti-aliasing filter is at least a 6th order elliptic filter with its cutoff at 5KHz. *(The specifications on the sampling frequency may change as a result of loading analysis on the hardware.)*

The A2D generates an interrupt to the DSP processor upon completion of a conversion cycle. The conversion result is mapped into the DSP memory space.

8.3 Input Gain

An input gain stage must be provided to scale the input voltage to optimize the A2D range. This input gain stage must have at least three settings, under control of the microprocessor.

8.4 DSP

The core hardware provides a TMS320C31, operating at 40MHz.

8.5 RAM

RAM is provided for both code and data. 1MByte of zero-wait state memory, organized as 512K x 16, is the minimum required. It should be expandable up to 4MBytes or more.

8.6 ROM

A 32KByte boot ROM must be provided.

*(This size is based on the commonly available PROM size.)*

8.7 Dual Port RAM

At least 8KByte of Dual Port RAM, organized as 4K x 16, must be provided for inter-processor communication.

AVI XP Core Functional Specificaton

ACUSON CONFIDENTIAL

8.8 Interprocessor Synchronization

To support synchronization between the Core and the Executive, at least 8 semaphore flags must be provided. These allow for the Core and the Executive to arbitrate resources in the dual port RAM and pass messages between them.

In addition, two asynchronous interrupts must be provided. One to interrupt the Executive from the Core, and the other to interrupt the Core from the Executive.

9. Enhancements

A number of enhancements to the Core speech recognition may be desirable. This will not be fully understood until the system development has proceded further. However, the possibilities are outlined here, as best as they are understood.

9.1 Noise Cancellation

It may be desirable to add some noise cancellation capability to the input data stream. This would be executed in the DSP algorithms. The primary goal would be to minimize the corrupting effect of doppler noise on the spoken commands. An additional goal would be to minimize background environmental noise.

9.2 Post-Processing

Another possible enhancement that might be required is to implement some post-processing on the recognition results. In the event that a given vocabulary contains words that are known *a priori* to be confusable, then some additional feature checking and decision making might be included to improve their distinction. This will only be known after the final vocabulary is understood and checked.

9.3 Audio Output

It might be desirable to support audible prompts to the operator. If that is the case, it would be implemented as part of the Core Module using pre-recorded prompts.

The Core hardware would be expanded to support a digital to analog converter. It would operate at the same sampling frequency as the input analog to digital converter. The software and interface specifications would be expanded to support messages from the Executive to download the pre-recorded data and to select which is to be played back to the operator. This might require a decompression capability.

The requirements for this will only be known as the full system is more completely defined.

AVI XP Core Functional Specificaton

APPENDIX 3

ACUSON VOICE INTERFACE

ON THE 128/XP:

SUBSYSTEM ARCHITECTURE REQUIREMENTS

*REVISION 1.2*

June 5, 1995

Responsible Engineer

Dan Need

1. Table of Contents

1. TABLE OF CONTENTS — 2

2. SCOPE — 4

3. REVISION HISTORY — 4

4. APPLICABLE DOCUMENTS — 4

5. GLOSSARY OF TERMS — 4

6. VISION — 5

7. FUNCTIONAL OVERVIEW — 5

8. FUNCTIONAL REQUIREMENTS — 6

8.1 SPECIFIC CLINICAL APPLICATIONS — 6
    8.2 SPEED OF OPERATION — 6
    8.3 RECOGNITION PERFORMANCE — 6
    8.4 NUMBER OF USERS — 7
    8.5 TRAINING AND CUSTOMIZATION — 7
    8.6 INTEGRATION WITH USER INTERFACE — 7
    8.7 CONFIGURATION OPTIONS — 7
    8.8 COMPATIBILITY — 7

9. DETAILED REQUIREMENTS — 8

9.1 USER INTERFACE — 8
        9.1.1 ACTIVATION — 8
        9.1.2 HELP INTERFACE — 8
        9.1.3 USER-SETUP — 9

AVI XP Subsystem Architecture

| | |
|---|---|
| 9.1.4 TRAINING INTERFACE | 9 |
| 9.1.5 SPECIAL MODES | 9 |
|    9.1.5.1 DGC Control | 9 |
| 9.2 MODULE INTERFACES | 9 |
| 9.2.1 EXECUTIVE ⇔ SYSTEM | 9 |
| 9.2.2 EXECUTIVE ⇔ CORE | 10 |
| 9.3 HARDWARE | 10 |
| 9.3.1 MICROPHONE | 10 |
|    9.3.1.1 Wired | 10 |
|    9.3.1.2 Headset | 10 |
|    9.3.1.3 Perfomance Characteristics | 10 |
| 9.3.2 EXECUTIVE | 10 |
| 9.3.3 CORE | 11 |
| 9.3.4 SYSTEM | 11 |
| 9.4 SOFTWARE | 11 |
| 9.4.1 CORE | 11 |
|    9.4.1.1 Signal Conditioning | 12 |
|    9.4.1.2 Audio Output | 12 |
|    9.4.1.3 Training | 12 |
|    9.4.1.4 Recognition | 12 |
| 9.4.2 EXECUTIVE | 12 |
|    9.4.2.1 Voice Control | 12 |
|    9.4.2.2 Active Sub-Vocabulary Control | 12 |
|    9.4.2.3 Command Mapping | 12 |
|    9.4.2.4 System State Tracking | 12 |
|    9.4.2.5 Voice Template Management | 13 |
|    9.4.2.6 Speaker-Independence | 13 |
|    9.4.2.7 Audio Output | 13 |
| 9.4.3 SYSTEM | 13 |
|    9.4.3.1 Command Execution | 13 |
|    9.4.3.2 System State Tracking | 13 |
|    9.4.3.3 User-Interface Support | 13 |
| 9.5 VOCABULARY | 13 |

2. Scope

*This document is a framework to begin discussion and highlight areas requiring further work. It does not purport to be the final specification of a Voice Interface on any Acuson ultrasound system.*

This document describes the overall architecture of Acuson Voice Interface subsystem as implemented on the 128 and XP. The functional divisions between each component of the subsystem, as well as the requirement of each, are outlined. Additional documents specify the requirments of each component of the complete subsystem.

3. Revision History

| Revision | Date | Description |
|---|---|---|
| 0.1 | 10/31/94 | First preliminary draft. |
| 0.2 | 11/17/94 | Second preliminary draft. Distributed for feedback. |
| 1.0 | 11/29/94 | General clean up; focuses on Executive-intensive design; enhances discussion of Executive/Core. |
| 1.1 | 11/29/94 | Correct typographical errors. Correct document cross-references. |
| 1.2 | 06/05/95 | Correct more typographical errors. |

4. Applicable Documents

This specification provides an overview of the entire Acuson Voice Interface subsystem, as implemented on the XP and 128. The following documents describe in more detail the various components.

- Acuson Voice Interface on the 128/XP: Core Functional Specification
- Acuson Voice Interface on the 128/XP: Executive Functional Specification *(not completed)*
- Acuson Voice Interface on the 128/XP: Core/Executive Interface Specification
- Acuson Voice Interface on the 128/XP: Vocabulary Specification

5. Glossary of Terms

| | |
|---|---|
| *Active Sub-Vocabulary*: | The sub vocabulary which is actively being searched to match a received utterance. |
| *ASR*: | Automatic Speech Recognition. |
| *Discrete Utterance*: | Class of ASR in which the spoken commands must be separated by discrete pauses in the speech pattern. Each connected phrase is handled by the ASR system as a single spoken command. |
| *Connected Speech*: | Class of ASR in which commands can be spoken naturally in the midst of flowing speech. |
| *Raw Recognition Performance*: | Measure of the basic accuracy of the ASR system. Counts the number of correct recognitions on the spoken vocabulary. Expressed as a percentage: $correct/attempted \times 100\%$. |

ACUSON CONFIDENTIAL

*Speaker Dependent*: Class of ASR in which the system must be trained to the operators voice patterns. Typically the operator must train the system by speaking each possible command to be recognized a number of times. The amount of training required varies, but is typically between 3 and 7 spoken iterations.

*Speaker Independent*: Class of ASR which requires no training by the particular operator before it can recognize commands successfully.

*Sub-Vocabulary*: A defined subset of the complete vocabulary that can be referenced as a unit.

*Templates*: Patterns corresponding to a vocabulary command in a particular voice.

*Vocabulary:* The defined set of commands to which the ASR system seeks to match a spoken word, by comparing to the templates of the active voice.

*Voice*: The vocabulary as spoken by a particular speaker. At any one time, a single voice is active, and the ASR system matches spoken commands against the vocabulary in that particular voice.

6. Vision

The Acuson Voice Interface is a targeted voice interface to be added to the XP or 128 as an upgrade. It provides speech-based, hands-free control of the ultrasound machine designed to meet the needs of specific clinical applications. The Voice Interface will operate in parallel with the keyboard, allowing the operator to control the machine seamlessly by both voice and keyboard.

7. Functional Overview

The Acuson Voice Interface allows the operator to control the ultrasound machine by spoken commands, using a tethered headset microphone. The Voice Interface operates in conjunction with keyboard control.

The Voice Interface implements speaker-dependent discrete-utterance speech recognition. Some tailoring may be required between widely different languages. However, within the same language, any speaker can train the system to their specific voice and use it successfully.

Eventually, the Voice Interface supports evolution to a speaker-independent solution. At first, this may be a local speaker-independence, created from the distribution of operators at the particular laboratory. As much as possible, the system design should accomodate that evolution.

The Voice Interface is implemented in this modular manner:

ACUSON CONFIDENTIAL

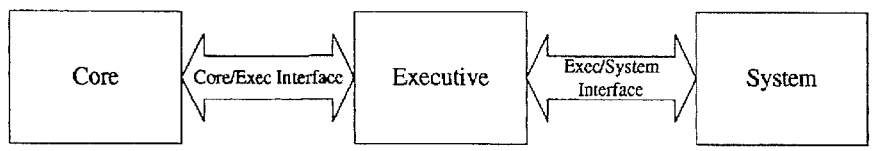

Figure 1: Modular Implementation of Voice Interface

- The Core Module implements the basic automatic speech recognition.
- The Executive Module controls the operation of the Core Module, receives from the Core Module the recognized commands, and communicates the required operation to the System.
- The System communicates with the Executive Module to synchronize the Voice Interface with the state of the ultrasound machine.

A finite set of defined commands and responses between the Executive and the System, and between the Executive and the Core allow the seamless integration of the entire Voice Interface with the normal operation of the ultrasound machine.

The Acuson Voice Interface is not directly mapped to the keyboard. It may support commands that are not simple keystrokes. Conversely, all the capability of the keyboard may not be included in the Voice Interface.

The Voice Interface can be added as an upgrade to any 128 or XP. All that is required is the available serial port, the voice interface module, the cosmetic upgrade to support the microphone jack, and the associated upgrade to Syscon. The future capability of the Acuson Voice Interface can be upgraded by simple software changes.

8. Functional Requirements

8.1 Specific Clinical Applications

The Acuson Voice Interface is primarily designed to substantially meet the needs of specific clinical applications. A subset of generic machine control is required for each application. As the suite of clinical applications addressed by the Voice Interface grows, so will the generic control of the machine. The applications targeted are:
- Intra-caviteal exams (endo-rectal, endo-vaginal, trans-esophogeal)
- Sterile field exams
- Surgical exams
- *... Need to define a set to pursue.*

8.2 Speed of Operation

The addition of the Acuson Voice Interface must not noticeably slow down the transition times on the system. The total delay between the speaking of a command and the initiation of the activity on the ultrasound machine must not be more 150msec.

8.3 Recognition Performance

There are two aspects to the recognition performance of the Voice Interface.

AVI XP Subsystem Architecture

ACUSON CONFIDENTIAL

- It must correctly recognize the defined commands (raw recognition rate).
- It must not recognize general conversation as commands to the system (substitution errors).

The raw recognition rate must meet or exceed 98%. Testing for this is specified in "Acuson Voice Interface on the 128/XP: Core Functional Specification."

There is no formal testing defined for substitution errors.

8.4 Number of Users

The Voice Interface must support up to $N$ separate operators. Non-volatile storage must be provided to store the training of these voices. The operator can then select which voice to use, or train up their own voice.

In addition to the $N$ voices in non-volatile storage, an additional voice must be allowed in volatile storage, so that a random operator not among the $N$ stored in the system can still train up the system and use it.

An additional feature must be provided by which the Acuson Voice Interface can create a composite voice out of the $N$ trained voices. This creates a site-specific speaker-independent mode of operation.

*Note that the required number of users is also an open-loop guess. This should be determined based both on cost of mass storage and the expected or ordinary number of operators in a given laboratory. It could also be handled as a configuration option.*

8.5 Training and Customization

The training procedure should not require the operator to repeat each command more than 7 times. When training, the operator should be able to skip training of a given word or subset of the vocabulary, update training, or provide a completely new training sequence.

The operator must have the ability to
1. select from among the trained voices.
2. train and save a new voice.
3. create a new voice from a user-defined subset of the trained voices.

*(Note that this requirement on number of repetitions is again an open-loop guess. There is some maximum number of repetitions beyond which the operator will quickly tire of using the machine. What that is can be established through clinical trial.)*

8.6 Integration with User Interface

The Acuson Voice Interface must be integrated with the screen display of the ultrasound. This integration must provide:
- Indication to the operator when the Acuson Voice Interface is active.
- Method by which the operator can configure the system for their own voice and train the vocabulary.
- Method by which the operator can receive help to prompt for allowed commands.
- Feedback as to the state of the DGC adjustment, when the potentiometers are modified by the Voice Interface.

8.7 Configuration Options

*TBD*

- Variable number of users, depending on amount of permanent memory purchased??
- Wireless microphone??
- Others??

8.8 Compatibility

AVI XP Subsystem Architecture

ACUSON CONFIDENTIAL

*TBD*

This will depend on mechanical design choices, as well as physical interface choices.
- CSI3??
-

9. Detailed Requirements

9.1 User Interface

The Acuson Voice Interface is a new interface modality to the ultrasound machine. It will operate in parallel to the existing methods of controlling the Acuson by keyboard and footswitch. With it, the user will have a multi-modal interface.

The Acuson Voice Interface is not constrained to be a keyboard replacement. In cases in which the keyboard control model does not translate into intuitive voice control, the Voice Interface attempts to match the operator's intuitive model of machine control.

9.1.1 Activation

The Voice Interface can be in three different activation states:
- *OFF*:   completely disengaged. Control of the machine is only via the keyboard.
- *PASSIVE*:   engaged, but in a passive state such that it is not controlling the machine. All control commands are ignored, except the single verbal command to take it to the active state.
- *ACTIVE*:   engaged and actively controlling the machine. If control commands are recognized, the appropriate action is taken.

At system power-up the Voice Interface is in the OFF state. The user puts it into the PASSIVE state by using keyboard control. At any time, the Voice Interface can be returned to the OFF state by means of the keyboard control.

*Suggestion: a code key defined to enable the Voice Interface or disable it.*

In the PASSIVE state, the Voice Interface is only capable of recognizing the single command ("activate" or something similar) to move it into the ACTIVE state. This transition can only be made by the verbal command.

In the ACTIVE state, the Voice Interface is actively listening for commands and controlling the machine based on recognized commands. It can be placed back into the PASSIVE state only by the verbal command ("deactivate" or something similar).

*Suggestion: it may be beneficial to allow the user to move between ACTIVE and PASSIVE states using keyboard control.*

The state of the voice interface must be communicated to the user in some manner via the monitor.

*Suggestion: a voice interface icon, which is absent in the OFF state, present and de-hilighted in the PASSIVE state, and present and hilighted in the ACTIVE state.*

9.1.2 Help Interface

A mechanism must be provided by which the user can be prompted for the allowed commands. This would display all the commands which are active at the time of the request for help. The help display would be removed at the receipt of the next verbal command, or the next keyboard action.

*Suggestion: a scrolling window displayed on the monitor listing the active commands. Similar to the interface for the automatic annotation.*

AVI XP Subsystem Architecture

*Another possibility would be to remove the image and fill the text screen with a display of all the allowed commands. Removing the image, however, might be objectionable.*

*Still another possibility is to have no help, or a spoken help only, or a cue-card help.*

9.1.3 User-Setup

A mechanism must be provided by which the user can configure the voice interface. This must include the ability to:
- activate the voice interface.
- select which voice to use.
- train a voice.
- set system parameters, such as sensitivity.

The operator must be able to save personal settings as part of the full-recall.

9.1.4 Training Interface

An interface must be provided by which the user can train the selected voice to the vocabulary. This includes the ability to skip a vocabulary word, train it, or update the existing training. Training/updating may require multiple iterations for speaking the word. Feedback must be provided to the user that an iteration was successful or not.

*Suggestion: How this can be implemented may depend on the resources in Syscon.*

> *A possibility for a complete interface might be to display the entire active vocabulary structure on the screen (as is done for the annotation function) and allow the user to select with the trackball which command to train. Softkeys would define the operation of training or updating. A small field in the screen would display the training/updating iteration and provide success or failure feedback. For this to work, Syscon must have complete knowledge of the vocabulary content and structure.*

> *A possibility for a minimal interface might be to display only a single command. Softkeys would still define the operation of training, updating, or skipping. The training/updating information would still need to be displayed. The advantage of this is that Syscon does not have to know the vocabulary content and structure.*

> *Training or updating previous training can be done on a global basis, so that all of the words must be either updated or trained.*

9.1.5 Special Modes

There are some special modes in the voice interface that require some defined changes in the screen format.

9.1.5.1 DGC Control

When the DGC pots are under voice control, feedback must be provided to the user as to the current DGC curve.

*Suggestion: apparantly when in RES the pots no longer match the screen display, and this is not objectionaable to the operator. May follow that model.*

9.2 Module Interfaces

9.2.1 Executive ⇔ System

AVI XP Subsystem Architecture

The interface between the Executive and the System is an RS-232 serial link, operating at 19600 baud. It allows the Executive to issues commands to the System, as well as query the operational state of the System. The System can also initiate communication to the Executive to inform it of changes in the operational state of the System, or training and user-setup parameters.

This interface is expected to be accomplished using a new design. For a complete description, see the <additional document>.

9.2.2 Executive ⇔ Core

The Core Module sits directly on the processor bus of the Executive. The two modules interface directly through shared memory space. This interface allows the Executive to control the recognition and training processes on the Core, and provides the mechanism by which the Core communicates the recognized commands to the Executive.

See <additional document> which fully describes the interface.

9.3 Hardware

As much as possible, the hardware required for the Voice Interface is selected from readily available third-party suppliers. By conforming to industry standards, a variety of suppliers are available, and compliance is guaranteed.

9.3.1 Microphone

The microphone input will be provided by a wired, headset, dynamic microphone The Voice Interface will only support the microphone eventually selected.Possible OEM's for good quality microphones used in the industry for speech recognition applications are Shure, Audio Technica, and Telex.

9.3.1.1 Wired

The primary microphone will be connected directly to the System. The cord will be approximately as long as the transducer cables. The input for the microphone is provided by a new microphone input jack. Ideally, it should be placed on the front of the system, such that the microphone cable can easily be managed along with the transducer cables. A wireless microphone is not considered to be a requirement for the XP product.. *(This may be incorrect, given the concerns about operating room operation.)*

9.3.1.2 Headset

The microphone will mount on the operator with a headset. This will hold the element rigidly in place, close to the operators mouth. Some possibilities for headsets are full assemblies that mount over the entire head, or minimal ear mounting supportes.

9.3.1.3 Perfomance Characteristics

The frequency response must extend beyond 10KHz.

The microphone must be direction, with noise-cancelling built in.

9.3.2 Executive

The Executive will be designed around an embedded AT-class PC conforming to the PC/104 or STD standard. Currently it is expected that it will require a 286 processor. It must have RS-232 capability, as well as non-volative mass storage for the voice templates, as well as the firmware.

Permanent storage requirements depend on the ultimate choice for a Core technology. An outside estimate is <amount>/vocabulary word/voice. This storage may be provided in at least two ways:
1. FLASH-based fixed-disks on the embedded PC.
2. FLASH-cards which the operator carries around with themselves.

ACUSON CONFIDENTIAL

See the specification for the Executive Module for the complete requirements.

9.3.3 Core

The Core ASR algorithms will run on a custom DSP card. As a minimum, this will provide a TMS320C31 DSP processor operating at 40MHz. At least one channel of audio input will be provided for the microphone. There may also be a requirement for a single channel of audio output for any audio prompts.

See the specification for the Core Module for the complete details of the hardware requirements.

9.3.4 System

The System level hardware requirements are to provide a place for all of the preceeding hardware to be housed. This includes the microphone input jack and the embedded PC for the Executive.

*Suggestion: Currently, there seem to be several possibilities for the jack:*

> *The side panel for the storage bin could be replaced. On the XP this could be either the left or right panel. For the 128, it would have to be the right panel?*
>
> *With a cosmetic change to the keyboard trim, it might be possible to get the mic jack into the push handle, on both the XP and the 128?*
>
> *Redesign the Physio panel to include a microphone jack?*
>
> *The mic jack could go into the back I/O panel?*

*Suggestion: Currently, there seem to be several possibilities for the embedded PC:*

> *Underneath the monitor beside the Audio Processor Board, there is space for a PC/104 style embedded PC. There are also mechanical mounts already there.*
>
> *On either side of the monitor there is also empty space to accomodate either a PC/104 or STD style embedded PC. In either case, mounting may be a problem.*
>
> *The removable storage panel on the right side of all machines could be redesigned to support the embedded PC. Room might be a problem then.*
>
> *There are available Scan Converter slots, but then the entire embedded controller must be a custom design, and we lose the advantages of developing of a PC platform.*

9.4 Software

As described in Section 7, Functional Overview, the implementation of the complete Acuson Voice Interface is distributed among the three separate modules. The Core is responsible for the underlying ASR. The Executive controls the recognition and training processes on the Core, and maps between the recognized voice command and the required System commands. The System executes the commands sent by the Executive and provides the only screen and keyboard interface to the user.

9.4.1 Core

The Core Module provides the fundamental ASR capability, as well as any additional signal conditioning that may be required on the input audio stream. It operates in two modes, training or recognition. In each case, the process is managed by the Executive. In the event the audio output is deemed necessary, the Core will also be responsible.

For a complete description of the functionality required to support the capabilities described here, see the ACUSON VOICE INTERFACE: CORE MODULE FUNCTIONAL SPECIFICATION.

9.4.1.1 Signal Conditioning

The Core may be tasked with some additional signal conditioning. This might include noise cancellation to address noisy backgrounds or Doppler noise in particular. Input gain control may be required to manage different operator volumes.

*These requirements are evolving still.*

9.4.1.2 Audio Output

If audio output is required, the Core will manage it. Under control of the Executive, it will output pre-recorded audio messages.

9.4.1.3 Training

In training mode, the Core detects an utterance and processes it to create a template for the command being trained. The processing might involve merging the new utterance with an existing trained template, or creating a completely new template. The success or failure of the training is reported to the Executive.

The Core is not responsible for any permanent storage of templates or managment of different voices.

9.4.1.4 Recognition

In recognition mode, the Core detects an untterance and attempts to recognize it against the currently active vocabulary. In the event of a successfull recognition, it reports back to the Executive the recognized command. If a failure of the recognition process is detected, this is also reported to the Executive.

9.4.2 Executive

The Executive module provides oversight of the Core Module and interfaces between the Core Module and the System.

9.4.2.1 Voice Control

The Executive module controls which voice templates are used by the Core Module to search for matching commands.

9.4.2.2 Active Sub-Vocabulary Control

The Executive module controls which subset of the vocabulary should be searched by the Core Module to find the matching command.

9.4.2.3 Command Mapping

Once a command from the active vocabulary is recognized, the Executive translates the desired action into the required commands to Syscon. This involves determining the state of the System, determining the required keystrokes or other commands to make the desired state change, and passing those commands to the System.

9.4.2.4 System State Tracking

The Executive must track the state of the ultrasound system. From this information, it determines which part of the vocabulary is active, as well as how to implement the desired commands.

ACUSON CONFIDENTIAL

9.4.2.5 Voice Template Management

The Executive is responsible for managing the permanent storage of the trained templates for each voice.

9.4.2.6 Speaker-Independence

This modular architecture does allow for an evolution to varieties of speaker independence, assuming that the Speaker-Independence is based on an aggregated set of templates, built from templates aquired for individual voices. The Executive will manage the aggregation of the various templates, and the recognition process, should it require multiple templates for a given command.

9.4.2.7 Audio Output

The Executive will determine which audio messages should be played back to the user and direct the Core to execute that.

9.4.3 System

The System software required to support the Voice Interface will be buried within Syscon. All communication between the Executive and the System occurs using the interface defined in Section 9.2.1, Executive ⇔ System.

9.4.3.1 Command Execution

The System must manage the implementation of the commands sent to it by the Executive. The scope of these commands are defined in the interface specification. In general, this includes all of the keyboard commands, as well as control of the analog gains.

9.4.3.2 System State Tracking

The System must track it's own state as it relates to the information required by the Executive. When queried by the Executive, this information must be returned.

9.4.3.3 User-Interface Support

The details specified in Section 9.1, User Interface, are all implemented within Syscon.

9.5 Vocabulary

The Acuson Voice Interface will have a defined vocabulary, which the user will be expected to use. The capability exists to later include macros defined by the operators, but the basic vocabulary is defined by Acuson. No mechanism exists to force the operator to speak the command specified, but it is assumed that they will cooperate. To encourage this cooperation, the vocabulary must be designed to be intuitive, and the training process must encourage cooperation.

The architecture described here supports a generic vocabulary of undefined size and complexity. This allows the final definition of the vocabulary to be deferred until late in the project, by which time it can be tightly defined through extensive clinical trials.

The general requirements on the vocabulary are that its design must support unlimited size. The total vocabulary is subdivided into subvocabularies which can be individually activated or deactivated. As the size of the active vocabulary increases, the system performance can be expected to decrease, both in recognition rate and speed of response.

The specific vocabulary definition is provided in ACUSON VOICE INTERFACE: VOCABULARY SPECIFICATION.

AVI XP Subsystem Architecture

What is claimed is:

1. A method for voice activation of an ultrasound system having a plurality of voice commands, comprising the steps of:

providing a group of voice commands for controlling the ultrasound system, said group including more than one sub-group of voice commands, wherein each of said sub-groups contains fewer number of voice commands than the group;

selecting at least one of said sub-groups;

deriving a signal from a spoken voice command using said selected at least one sub-group; and applying said signal to the ultrasound system to control the system.

2. The method of claim 1, said deriving step including recognizing a spoken voice command and translating said spoken voice command into said signal using said selected sub-group.

3. The method of claim 2, said translating step translating said spoken voice command into signals that are not codes of keystrokes of a keyboard.

4. The method of claim 1, further comprising using a non-voice device to control the ultrasound system.

5. The method of claim 4, wherein said using step uses a keyboard and/or footswitch to control the ultrasound system.

6. The method of claim 1, further comprising changing a state of the ultrasound system by a non-voice device.

7. The method of claim 1, said providing step being such that at least two of said sub-groups contain at least one common command.

8. The method of claim 1, said ultrasound system having a plurality of voice-command-determining-states, each of said states corresponding to at least one of said sub-groups, wherein said selecting step selects a sub-group that corresponds to an active voice-command-determining-state of the ultrasound system.

9. The method of claim 8, wherein the system can have a plurality of active voice-command-determining-states simultaneously, said selecting step selecting a plurality of sub-groups that correspond to the plurality of active voice-command-determining-states of the system and said deriving step derives said signal using said selected plurality of sub-groups.

10. The method of 8, said providing step providing sub-groups of commands so that a command for turning on a voice-command-determining-state of the ultrasound system and having the word "on" and another command for turning off such voice-command-determining-state and having the word "off" are in different sub-groups.

11. The method of claim 1, further comprising:

determining the actual state of the ultrasound system;

wherein said deriving step derives the signal also from the actual state of the ultrasound system.

12. The method of claim 11, wherein the determining step determines an active voice-command-determining-state of the ultrasound system, wherein said selecting step selects the at least one sub-group that corresponds to the active voice-command-determining-state of the ultrasound system determined in the determining step.

13. The method of claim 12, said method employing a control device, said determining step including the control device interrogating the active voice-command-determining-state of the ultrasound system.

14. The method of claim 12, said method employing a control device, said determining step including the ultrasound system automatically supplying its active voice-command-determining-state to the control device.

15. A method for voice activation of an ultrasound system, said method comprising the steps of:

providing a group of commands for controlling the ultrasound system;

determining the actual state of the ultrasound system;

deriving at least one signal from a spoken voice command using said group and based on the actual state of the ultrasound system;

applying the at least one signal to the ultrasound system.

16. The method of claim 15, wherein the system has a plurality of applications that can be active simultaneously, said deriving step including the steps of:

translating said spoken voice command into a first signal using said group;

creating a second signal when input resource of the system is allocated to an application unsuitable for receiving and acting upon said first signal;

supplying the second signal to the ultrasound system to cause the system to allocate input resource of the system to an application that is suitable to receive and act upon said first signal; and wherein said applying step applies the first signal to the ultrasound system after the input resource re-allocation.

17. The method of claim 15, said deriving step deriving said at least one signal from a desired state of the system indicated by the spoken voice command and the actual state of the system.

18. The method of claim 17, wherein said spoken voice command is "2-D" and the desired state is BMODE, wherein said deriving step derives a signal or signals that will turn off all other modes except for BMODE.

19. The method of claim 15, said method employing a control device, said determining step including the control device interrogating the state of the ultrasound system.

20. The method of claim 15, said method employing a control device, said determining step including the ultrasound system automatically supplying its state to the control device.

21. An apparatus for voice activation of an ultrasound system having a plurality of voice commands, comprising:

means for providing a group of voice commands for controlling the ultrasound system, said group including more than one sub-group of voice commands, wherein each of said sub-groups contains fewer number of voice commands than the group;

means for selecting at least one of said sub-groups;

means for deriving a signal from a spoken voice command using said selected at least one sub-group; and means for applying said signal to the ultrasound system to control the system.

22. The apparatus of claim 21, further comprising:

means for determining the actual state of the ultrasound system;

wherein said deriving means derives the signal based on the actual state of the ultrasound system, said determining means including a two way communication link.

23. An apparatus for voice activation of an ultrasound system, said apparatus comprising:

means for providing a group of commands for controlling the ultrasound system;

means for determining the actual state of the ultrasound system;

means for deriving at least one signal from a spoken voice command using said group and based on the actual state of the ultrasound system;

means for applying the at least one signal to the ultrasound system.

24. The apparatus of claim 23, said determining means including a two way communication link.

* * * * *

UNITED STATES PATENT AND TRADEMARK OFFICE
CERTIFICATE OF CORRECTION

PATENT NO. : 5,544,654
DATED : August 13, 1996
INVENTOR(S) : Murphy et al.

It is certified that error appears in the above-indentified patent and that said Letters Patent is hereby corrected as shown below:

In Column 4, line 34 replace:
"of the system of FIG. 9." with

--of the system of FIGS. 9 and 9A--

In Column 5, line 56 replace:
"$0<kv_n<1$ for all n." with

--$0<kn_n\leq 1$ for all n.--

In Column 8, line 7 replace:
"ence to FIGS. 9 and 9A or possibilities." with

--ence to FIGS. 9 and 9A for possibilities.--

Signed and Sealed this

Fourth Day of February, 1997

Attest:

BRUCE LEHMAN

Attesting Officer

Commissioner of Patents and Trademarks